(12) United States Patent
Denzinger et al.

(10) Patent No.: US 12,357,303 B1
(45) Date of Patent: Jul. 15, 2025

(54) SURGICAL STAPLER FOR SENSING AND COMMUNICATING TROCAR POSITION AND ANVIL STATE

(71) Applicant: CILAG GMBH INTERNATIONAL, Zug (CH)

(72) Inventors: Christopher Denzinger, Cincinnati, OH (US); Monica Rivard, Cincinnati, OH (US); Cory G. Kimball, Hamilton, OH (US); Matthew Corbin, Cincinnati, OH (US); Laura S. Downing, Cincinnati, OH (US); Matthew D. Cowperthwait, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/603,640

(22) Filed: Mar. 13, 2024

(51) Int. Cl.
| | |
|---|---|
| *A61B 17/072* | (2006.01) |
| *A61B 17/068* | (2006.01) |
| *A61B 17/34* | (2006.01) |
| *A61B 34/20* | (2016.01) |
| *A61B 90/98* | (2016.01) |
| *A61B 17/00* | (2006.01) |
| *A61B 17/115* | (2006.01) |
| *A61B 17/29* | (2006.01) |
| *A61B 34/30* | (2016.01) |

(52) U.S. Cl.
CPC .......... *A61B 17/072* (2013.01); *A61B 17/068* (2013.01); *A61B 17/07207* (2013.01); *A61B 17/34* (2013.01); *A61B 34/20* (2016.02); *A61B 90/98* (2016.02); *A61B 2017/00398* (2013.01); *A61B 2017/00477* (2013.01); *A61B 2017/07214* (2013.01); *A61B 2017/07221* (2013.01); *A61B 17/115* (2013.01); *A61B 2017/2927* (2013.01); *A61B 2017/348* (2013.01); *A61B 2034/2059* (2016.02); *A61B 34/30* (2016.02)

(58) Field of Classification Search
CPC ............ A61B 17/00234; A61B 17/068; A61B 17/0686; A61B 17/072; A61B 17/07207; A61B 17/115; A61B 17/1155; A61B 2017/00017; A61B 2017/00398; A61B 2017/00477; A61B 2017/07214; A61B 2017/00734; A61B 2017/2927; A61B 34/20; A61B 34/30; A61B 34/71; A61B 90/98
USPC .............. 227/19, 175.2, 176.1, 175.1, 180.1; 606/1, 139, 219
See application file for complete search history.

(56) References Cited

U.S. PATENT DOCUMENTS

| | | | |
|---|---|---|---|
| 7,918,377 | B2 | 4/2011 | Measamer |
| 8,657,174 | B2 | 2/2014 | Yates |

(Continued)

*Primary Examiner* — Scott A Smith
(74) *Attorney, Agent, or Firm* — TROUTMAN PEPPER LOCKE LLP

(57) ABSTRACT

The present disclosure provides a circular stapler. The circular stapler includes a stapling head assembly. A trocar is positioned at least partially within the stapling head assembly. An anvil is detachably attachable to the trocar. A knob rotatable to cause translation of the trocar to adjust a position of the anvil with respect to the stapling head assembly. One or more sensors are configured to generate data associated with a trocar position or an anvil state. A communication element is configured to provide the generated data to a hub, wherein the hub is configured to provide an indicator associated with the trocar position or the anvil state based on the generated data.

20 Claims, 38 Drawing Sheets

(56) References Cited

U.S. PATENT DOCUMENTS

| | | | |
|---|---|---|---|
| 9,913,642 B2* | 3/2018 | Leimbach | A61B 17/072 |
| 10,190,888 B2 | 1/2019 | Hryb | |
| 11,154,301 B2* | 10/2021 | Beckman | A61B 17/07207 |
| 11,185,331 B2 | 11/2021 | Adams | |
| 11,324,557 B2* | 5/2022 | Shelton, IV | A61B 17/0469 |
| 11,382,697 B2* | 7/2022 | Shelton, IV | G06F 3/04886 |
| 11,426,167 B2* | 8/2022 | Shelton, IV | A61B 90/96 |
| 11,622,763 B2* | 4/2023 | Parihar | A61B 17/115 227/176.1 |
| 11,737,749 B2* | 8/2023 | Shelton, IV | A61B 17/072 227/176.1 |
| 11,744,592 B2* | 9/2023 | Mozdzierz | A61B 17/1155 227/179.1 |
| 11,744,604 B2* | 9/2023 | Shelton, IV | A61B 17/07207 606/1 |
| 2011/0288573 A1 | 11/2011 | Yates | |
| 2013/0041371 A1 | 2/2013 | Yates | |
| 2017/0290583 A1 | 10/2017 | Reed | |
| 2018/0326144 A1 | 11/2018 | Truckai | |
| 2019/0200998 A1 | 7/2019 | Shelton, IV | |
| 2022/0233241 A1 | 7/2022 | Shelton, IV | |
| 2023/0138743 A1 | 5/2023 | Ross | |

\* cited by examiner

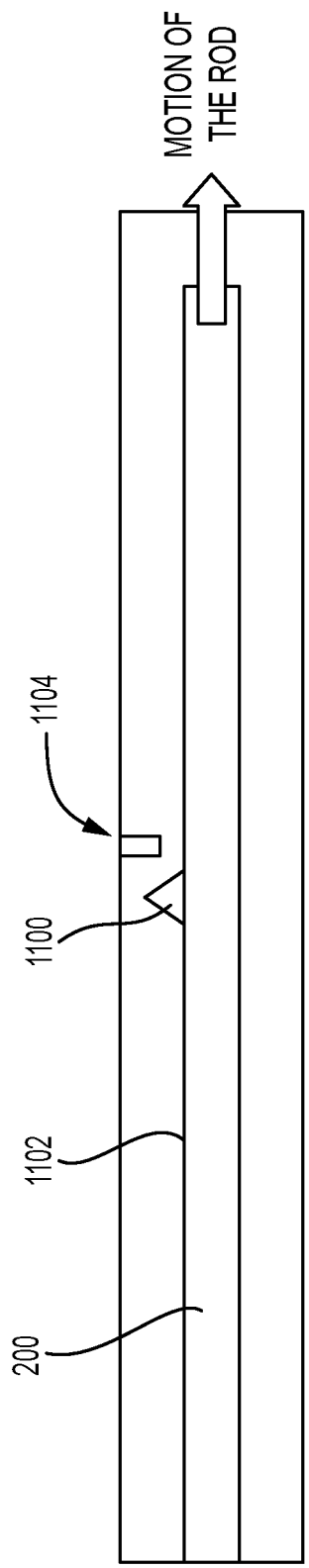
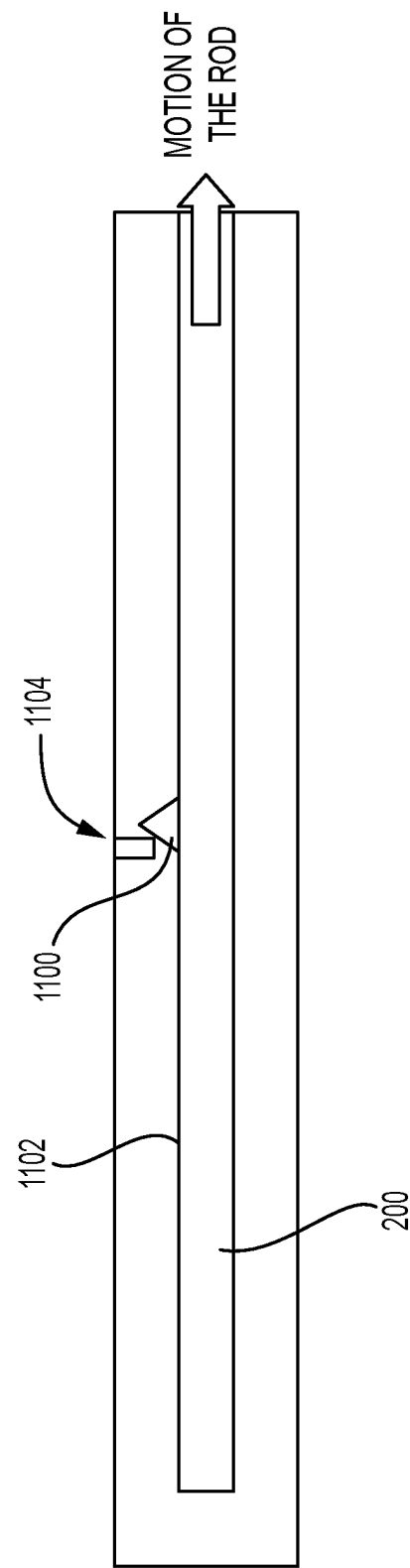

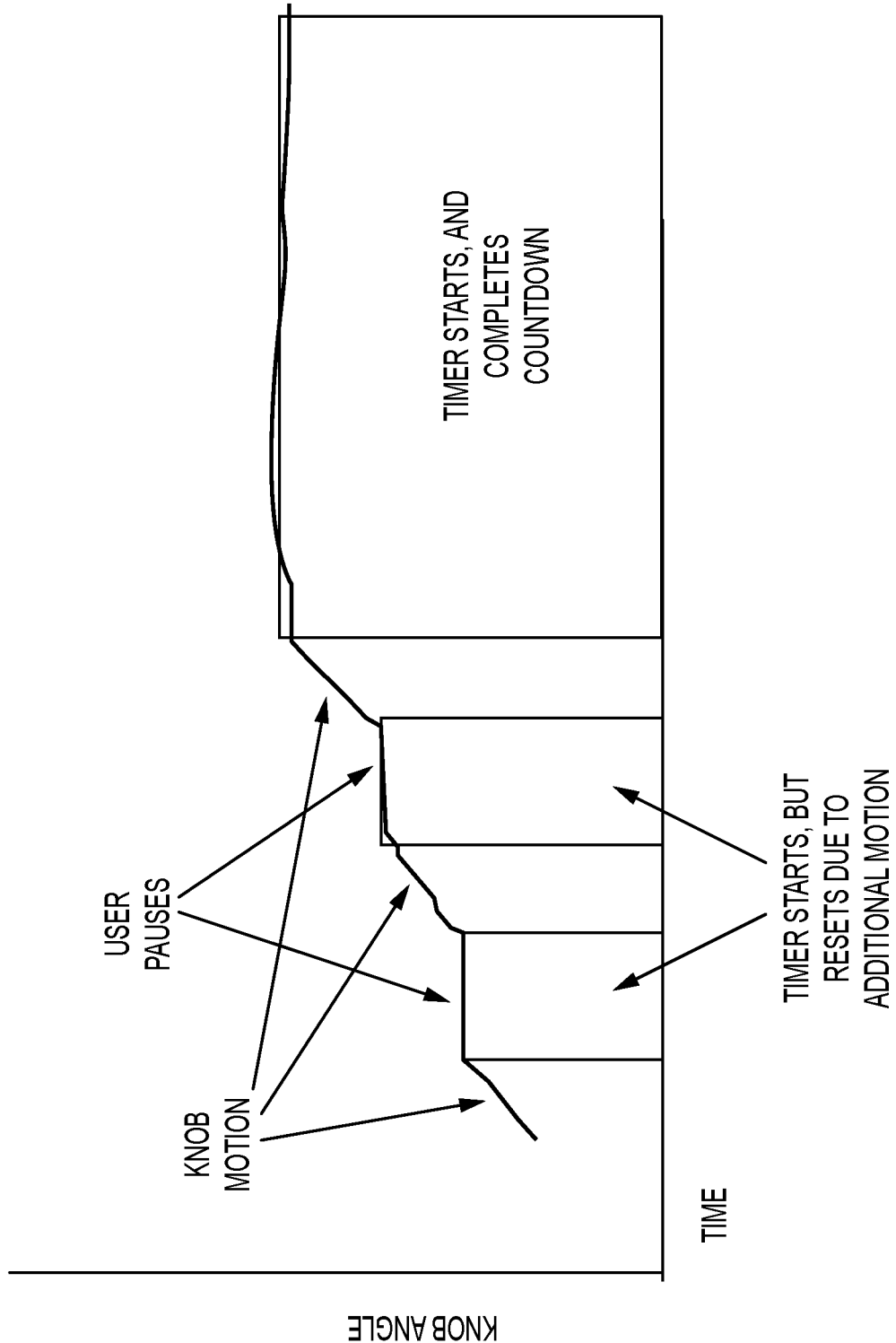

SURGICAL STAPLER FOR SENSING AND COMMUNICATING TROCAR POSITION AND ANVIL STATE

FIELD OF THE INVENTION

The present disclosure generally describes surgical instruments that can sense and communicate information related to operational status from the surgical instrument and, more particularly, to surgical staplers that can generate and communicate data related to trocar position to determinate an anvil state during use thereof.

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever the excess tissue on either end of the lumen that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Proper operation of the trocar (and the state of the anvil with respect to the trocar) is necessary in various aspects of operation of a circular stapler. For example, proper trocar retraction with an attached anvil clamps down on the tissue (device closing), which is critical for successful device firing and achieving a desired staple height. Further, proper trocar extension (device opening) is necessary to minimize tissue and anastomosis damage during remove of the circular stapler. Although circular staplers may have onboard visual indicators to provide the proper anvil state, the primary surgeon may not always have hands on the device or portions of the device may be visually obscured. A need exists, therefore, for improved circular stapler designs that can generate data for determining anvil state (based on position of the trocar) and communicate the data an external hub.

SUMMARY

The present disclosure provides solutions to the needs mentioned above. One aspect of the present disclosure provides an apparatus, such as a stapling apparatus. The apparatus can include a stapling head assembly. The apparatus can include a trocar positioned at least partially within the stapling head assembly. The apparatus can include an anvil detachably attachable to the trocar. The apparatus can include a knob rotatable to cause translation of the trocar to adjust a position of the anvil with respect to the stapling head assembly. The apparatus can include one or more sensors configured to generate data associated with a trocar position or an anvil state. The apparatus can include a communication element configured to provide the generated data to a hub, wherein the hub is configured to provide an indicator associated with the trocar position or an anvil state based on the generated data.

In any of the embodiments described herein, at least one of the one or more sensors can be a torque sensor configured to measure torque applied to the knob or a force sensor configured to measure force based on linear motion.

In any of the embodiments described herein, the knob can include one or more protrusions located on an outer circumference thereof. The apparatus can further include a fixed element located partially in a path of the one or more protrusions as the knob is rotated. The torque sensor can measure an increase in the measured torque magnitude when the one or more protrusions pass the fixed element. The trocar position or anvil state can be correlated with a number of the increases in the measured torque magnitude during rotation of the knob.

In any of the embodiments described herein, the indicator of the hub can display an open anvil state after a threshold number of increases in the measured torque after a firing of the apparatus.

In any of the embodiments described herein, the apparatus can further include one or more protrusions located on a surface of a linearly moveable element thereof. The apparatus can further include a fixed element located partially in a path of the one or more protrusions as the linearly moveable element is translated. The sensor can measure an increase in the measured torque magnitude or force magnitude when the one or more protrusions pass the fixed element and the trocar position or anvil state can be based on a number of the increases in the measured torque magnitude or force magnitude. The trocar position or anvil state can be correlated with the increases in the torque magnitude or force magnitude measurement.

In any of the embodiments described herein, the fixed element can be positioned such that the indicator of the hub displays an open anvil state based on the increase in the measured torque after a firing of the apparatus.

In any of the embodiments described herein, the fixed element can be positioned such that the indicator of the hub displays a home anvil state based on the increase in the measured torque prior to operation of the apparatus.

In any of the embodiments described herein, at least one of the one or more sensors can be a sensor configured to measure a rotational position of the knob.

In any of the embodiments described herein, the trocar position or anvil state can be correlated to the measured torque during rotation of the knob and the rotational position of the knob.

In any of the embodiments described herein, the apparatus further can include a controller that can be configured to: receive the generated data associated with the trocar position or anvil state from the one or more sensors; determine a fully closed anvil state based on the generated data; and provide an indicator of a start condition for a firing of the apparatus after a time delay based on the determined fully closed anvil state.

In any of the embodiments described herein, the indicator of the hub can display an unintentional motion indicator based on a change in the rotational position of the knob without a corresponding measured magnitude of torque.

In any of the embodiments described herein, the one or more sensors can be located in the knob.

In any of the embodiments described herein, the apparatus further includes a knob attachment configured to be coupled to the knob. One or more of the one or more sensors or the communication element can be located in the knob attachment. Another aspect of the present disclosure provides an apparatus, such as a stapling apparatus. The apparatus can include a stapling head assembly. The apparatus can include a trocar positioned at least partially within the stapling head assembly. The apparatus can include an anvil detachably attachable to the trocar. The apparatus can include a knob rotatable to cause translation of the trocar to adjust a position of the anvil with respect to the stapling head assembly. The apparatus can include two or more sensors comprising at least a torque sensor configured to measure torque applied to the knob and a sensor configured to measure a rotational position of the knob. The apparatus can include a controller configured to: receive torque and rotational position data from the two or more sensors; and determine a trocar position or an anvil state based on the received torque and rotational position data.

In any of the embodiments described herein, the controller can be configured to: determine a number of turns of the knob based on the received torque and rotational position data; and determine the trocar position or anvil state based on the number of turns of the knob.

In any of the embodiments described herein, the controller can be configured to: determine an open anvil state based on a threshold number of turns of the knob (130) after a firing of the apparatus.

In any of the embodiments described herein, the controller can be configured to: determine a fully closed anvil state based on the received torque and rotational position data; and provide an indicator of a start condition for a firing of the apparatus after a time delay based on the determined fully closed anvil state.

In any of the embodiments described herein, the controller can be configured to: determine an unintentional motion of the trocar based on a change in the rotational position of the knob without a corresponding measured torque; and provide a user alert based on the determined unintentional motion of the trocar.

Another aspect of the present disclosure provides an apparatus, such as a stapling apparatus. The apparatus can include a stapling head assembly having a staple deck surface. The apparatus can include a trocar positioned at least partially within the stapling head assembly. The apparatus can include an anvil having an anvil surface detachably attachable to the trocar. The apparatus can include a knob rotatable to cause translation of the trocar to adjust a gap between the anvil surface and the staple deck surface. The apparatus can include a knob attachment configured to be coupled to the knob. The apparatus can include one or more sensors located in the knob attachment configured to generate data associated with an anvil state based on the gap between the anvil surface and the staple deck surface. The apparatus can include a communication element configured to provide the generated data to a hub, wherein the hub is configured to provide an indicator associated with the anvil state based on the generated data.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 11A depicts a circular stapler having protrusions and a fixed element configured to provide an increased magnitude torque value or increased magnitude force value based on linear motion of the trocar caused by rotation of the knob in a first position, according to one aspect of the present disclosure;

FIG. 11B depicts the circular stapler shown in FIG. 11A in a second position, according to one aspect of the present disclosure;

FIG. 19 depicts a graph of rotational position of knob over time for initiating a firing sequence for the circular stapler shown in FIG. 8A, according to one aspect of the present disclosure;

Figure 1:
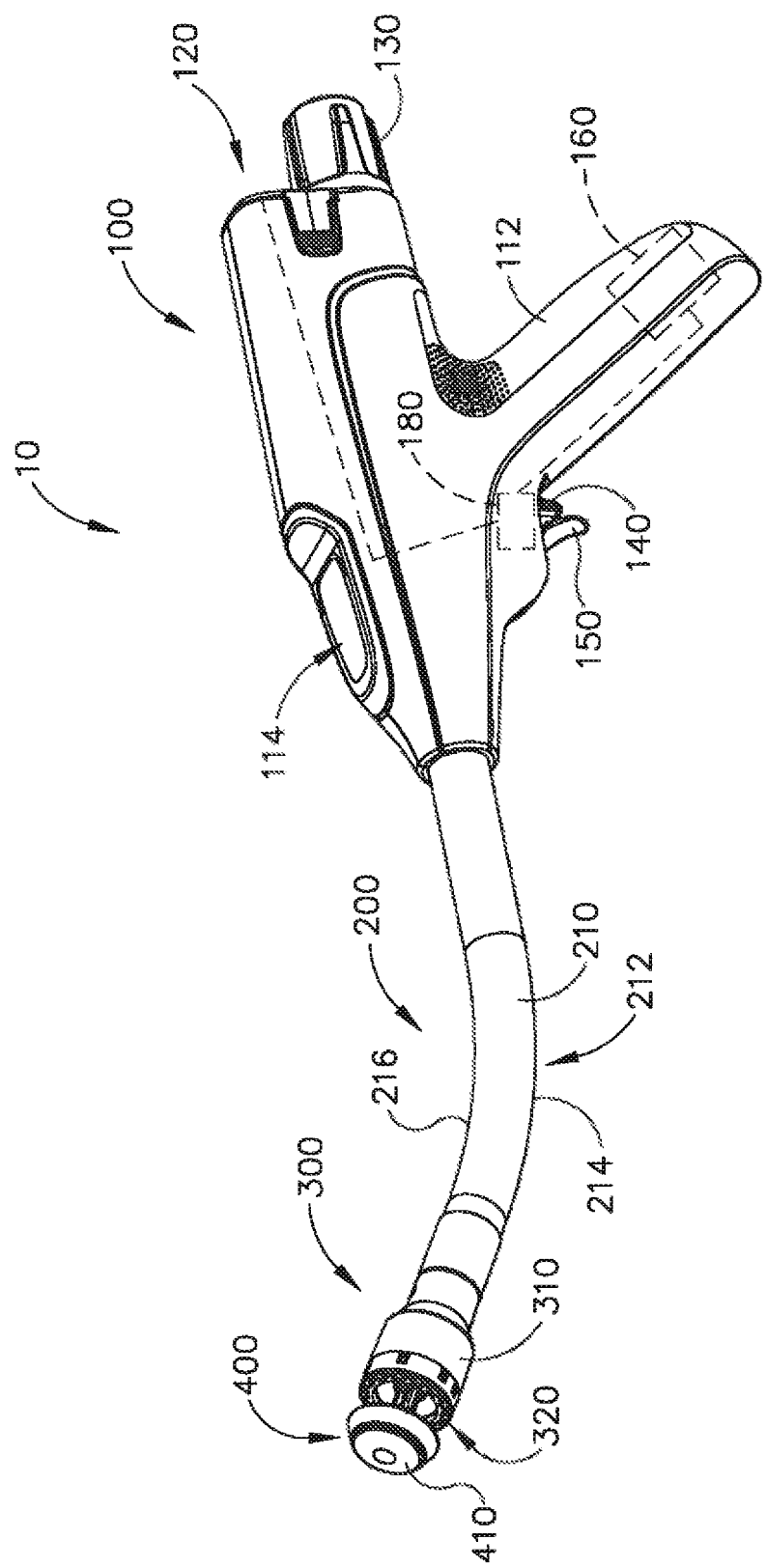
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
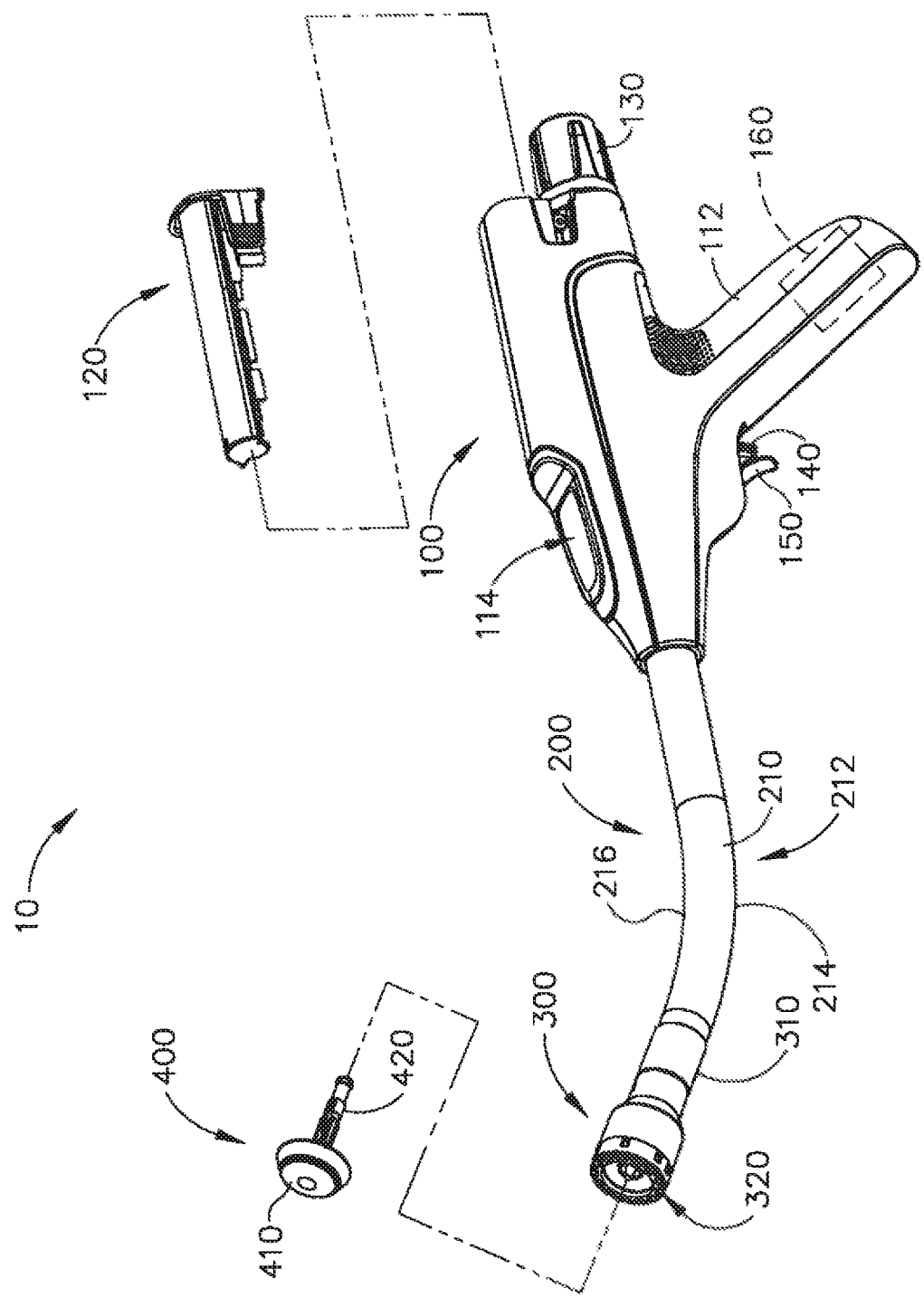
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), an anvil (400), and a removable battery pack (120). Each of these components will be described in greater detail below. It should be understood that, in addition to or in lieu of the following, instrument (10) may be further constructed and operable in accordance with at least some of the teachings of U.S. patent application Ser. No. 14/751,612, entitled "Method of Applying an Annular Array of Staples to Tissue," filed Jun. 26, 2015; U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

A. Exemplary Tissue Engagement Features of Circular Stapling Instrument

Figure 3:
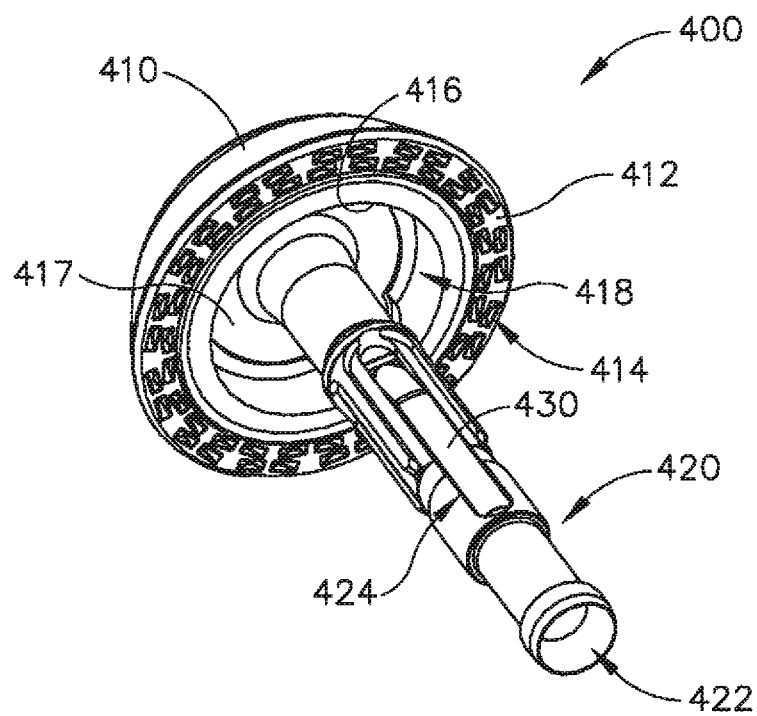
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Figure 4:
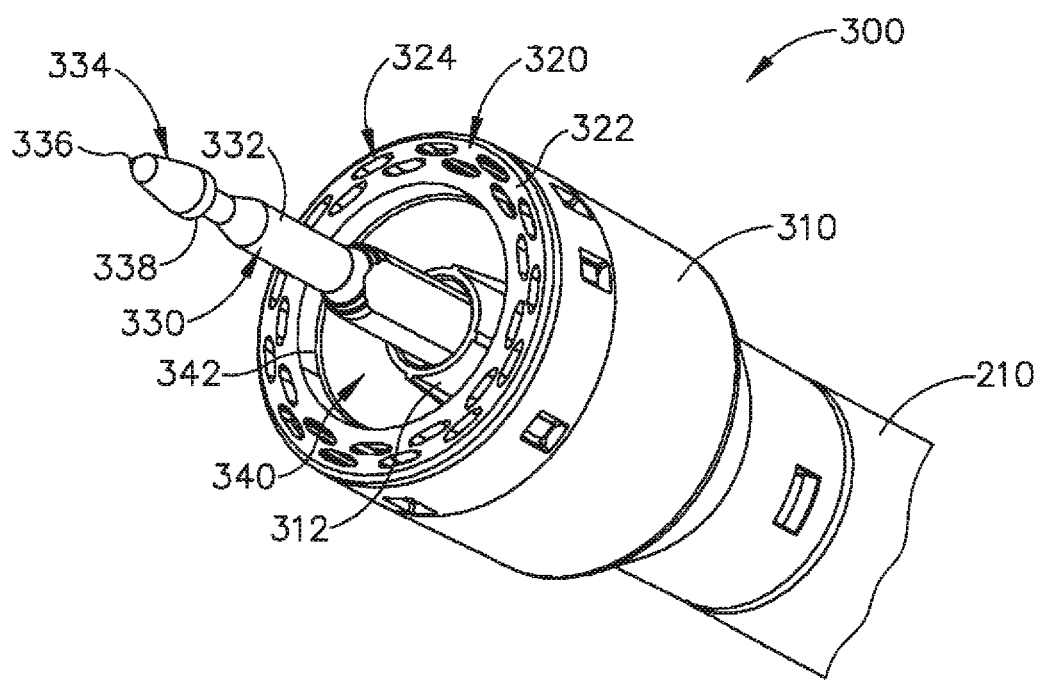
FIG. 4 depicts a perspective view of the stapling head assembly of the circular stapler of FIG. 1.
Figure 5:
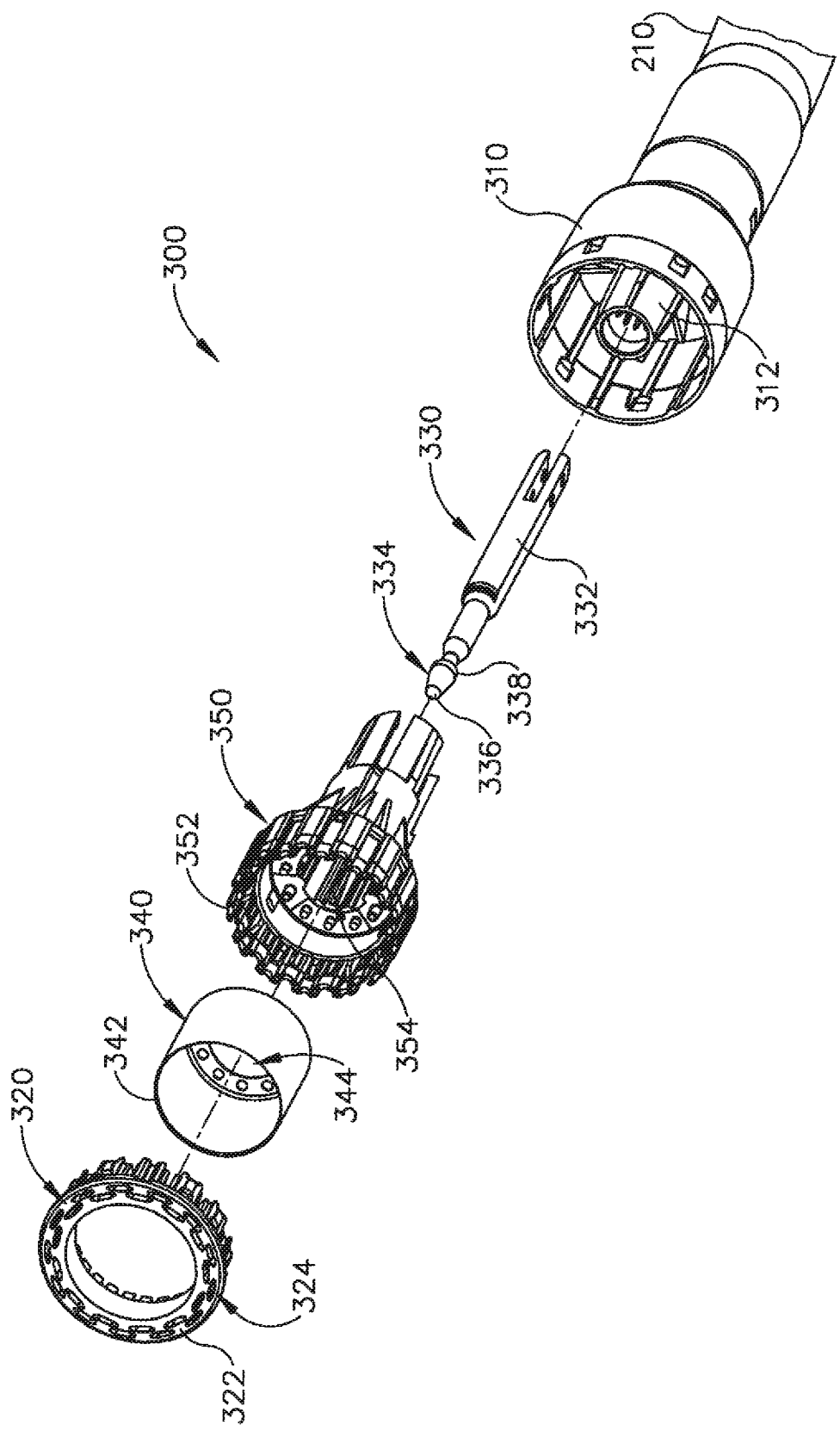
FIG. 5 depicts an exploded perspective view of the stapling head assembly of FIG. 4.

Stapling head assembly (300) is located at the distal end of shaft assembly (200). As shown in FIGS. 1-2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4-5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (420). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Deck member (320) defines an inner diameter that is just slightly larger than the outer diameter defined by knife member (340). Deck member (320) is thus configured to allow knife member (340) to translate distally to a point where cutting edge (342) is distal to deck surface (322).

Figure 6:
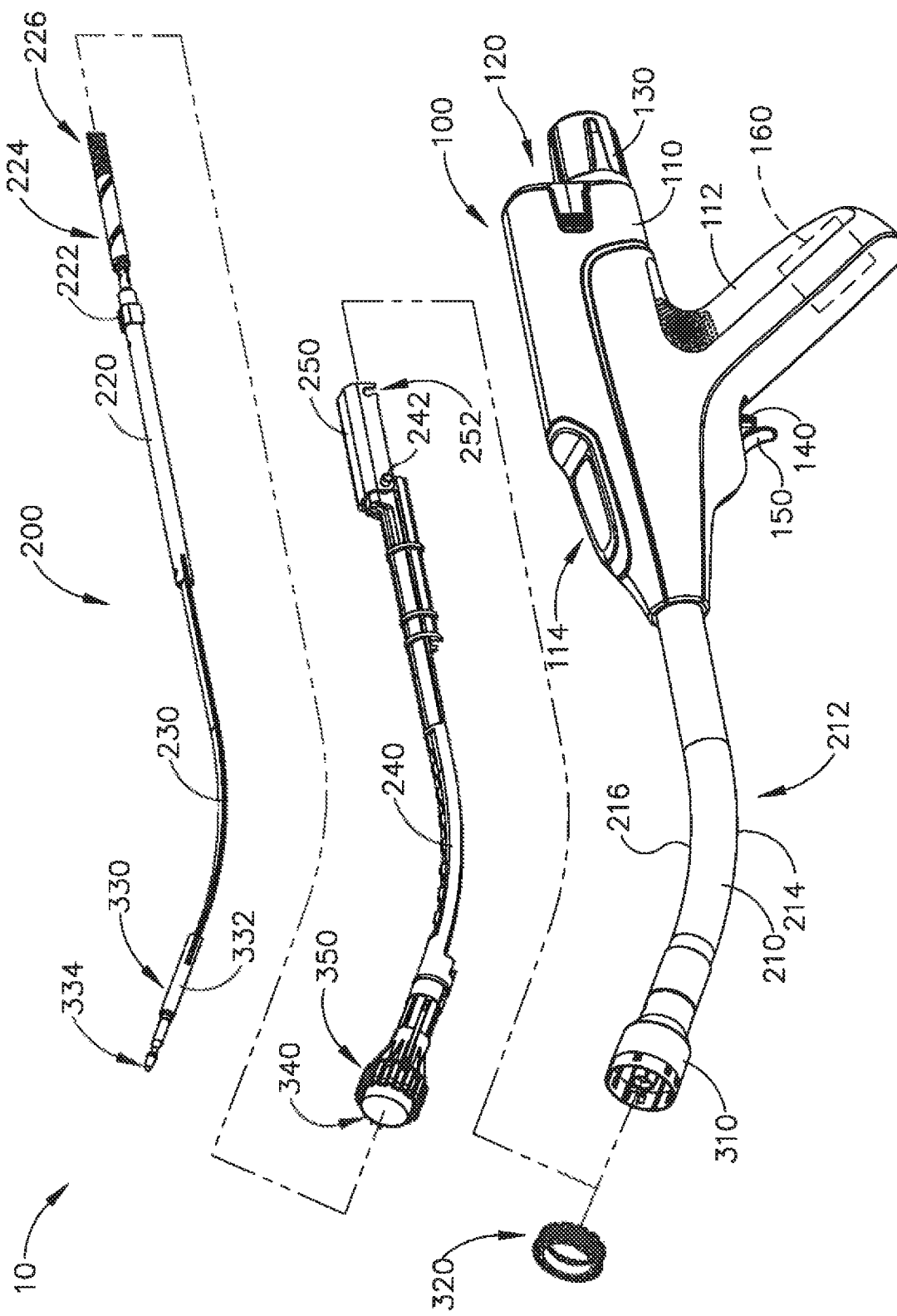
FIG. 6 depicts an exploded perspective view of the circular stapler of FIG. 1, with portions of the shaft assembly shown separately from each other.

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section (212) that is configured to facilitate positioning of stapling head assembly (300) within a patient's colon as described below. Curved section (212) includes an inner curve (216) and an outer curve (214).

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

B. Exemplary User Input Features of Circular Stapling Instrument

As shown in FIG. 1, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (500) away from stapling head assembly (300). Knob (130) may thus be used to adjust the gap distance between opposing surfaces (412, 322) of anvil (400) and stapling head assembly (300) until a suitable gap distance has been achieved.

In the present example, handle assembly (100) comprises a user feedback feature (114) that is configured to provide the operator with visual feedback indicating the positioning of anvil (400) in relation to stapling assembly (300). The operator may thus observe user feedback feature (114) while rotating knob (130), to confirm whether the suitable gap distance between anvil (400) and stapling assembly (300) has been achieved. By way of example only, user feedback feature (114) may be configured and operable in accordance with at least some of the teachings of U.S. patent application Ser. No. 14/751,612, entitled "Method of Applying an Annular Array of Staples to Tissue," filed Jun. 26, 2015, the disclosure of which is incorporated by reference herein. Other suitable forms of providing user feedback will be apparent to those of ordinary skill in the art in view of the teachings herein.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range.

In the present example, firing trigger (150) of the present example includes an integral actuation paddle, such as the paddle shown and described in U.S. patent application Ser. No. 14/751,231, entitled "Surgical Stapler with Reversible Motor," filed Jun. 26, 2015, the disclosure of which is incorporated by reference herein. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) as described in greater detail below.

Battery pack (120) is operable to provide electrical power to a motor (160) as noted above. Battery pack (120) may be removably coupled with handle assembly (100) through a snap fit or in any other suitable fashion. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery back (120) cannot be removed from handle assembly (100).

C. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
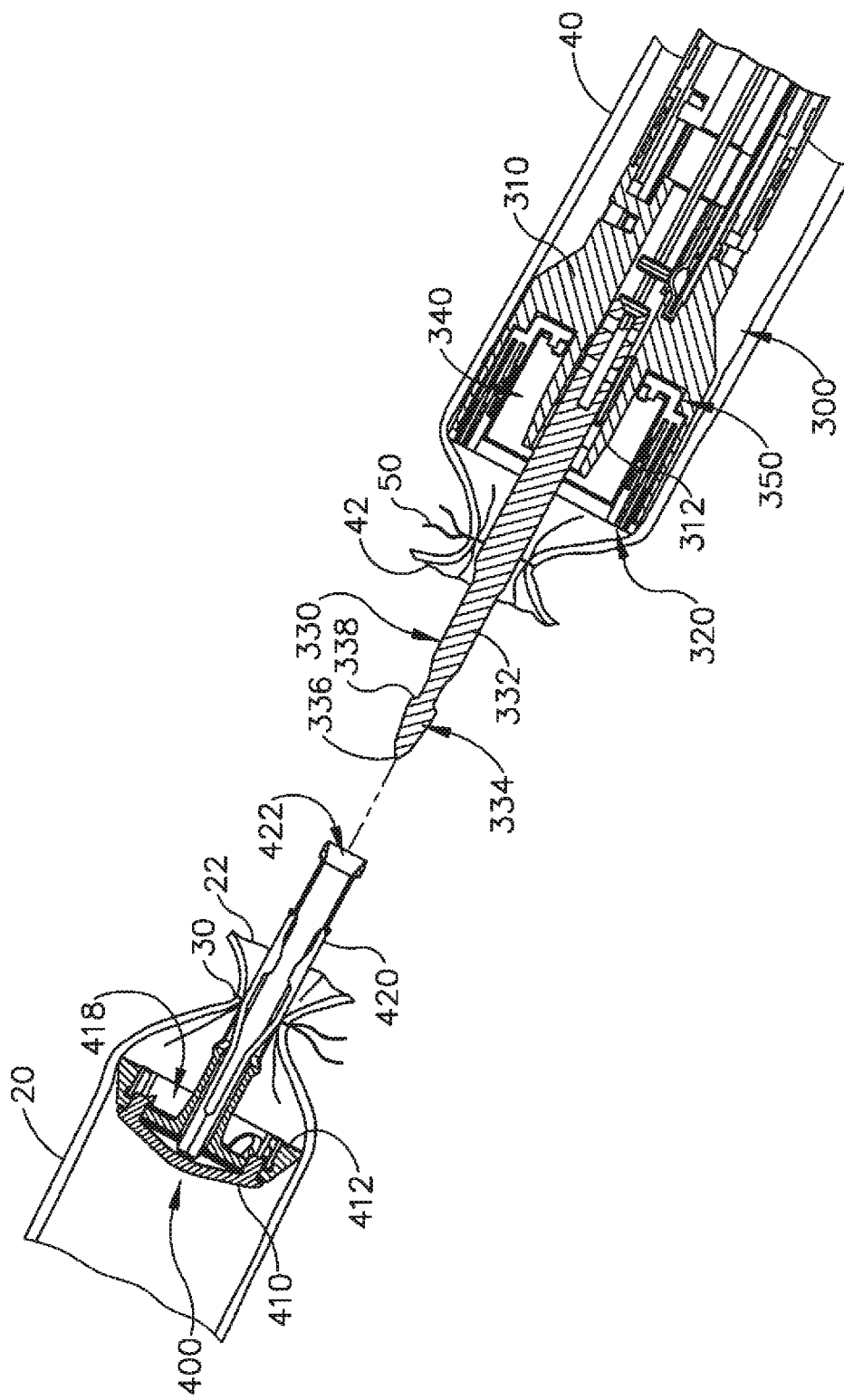
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. By way of example only, the surgical procedure may be performed laparoscopically in accordance with at least some of the teachings of U.S. Pub. No. 2016/0100837, entitled "Staple Cartridge," published Apr. 14, 2016, the disclosure of which is incorporated by reference herein; and/or U.S. patent application Ser. No. 14/864,310, entitled "Apparatus and Method for Forming a Staple Line with Trocar Passageway," filed Sep. 24, 2015, the disclosure of which is incorporated by reference herein. Various other suitable ways in which instrument (10) may be used to form an anastomosis (70) in a laparoscopic procedure will be apparent to those of ordinary skill in the art in view of the teachings herein.

As shown in FIG. 7A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Figure 7B:
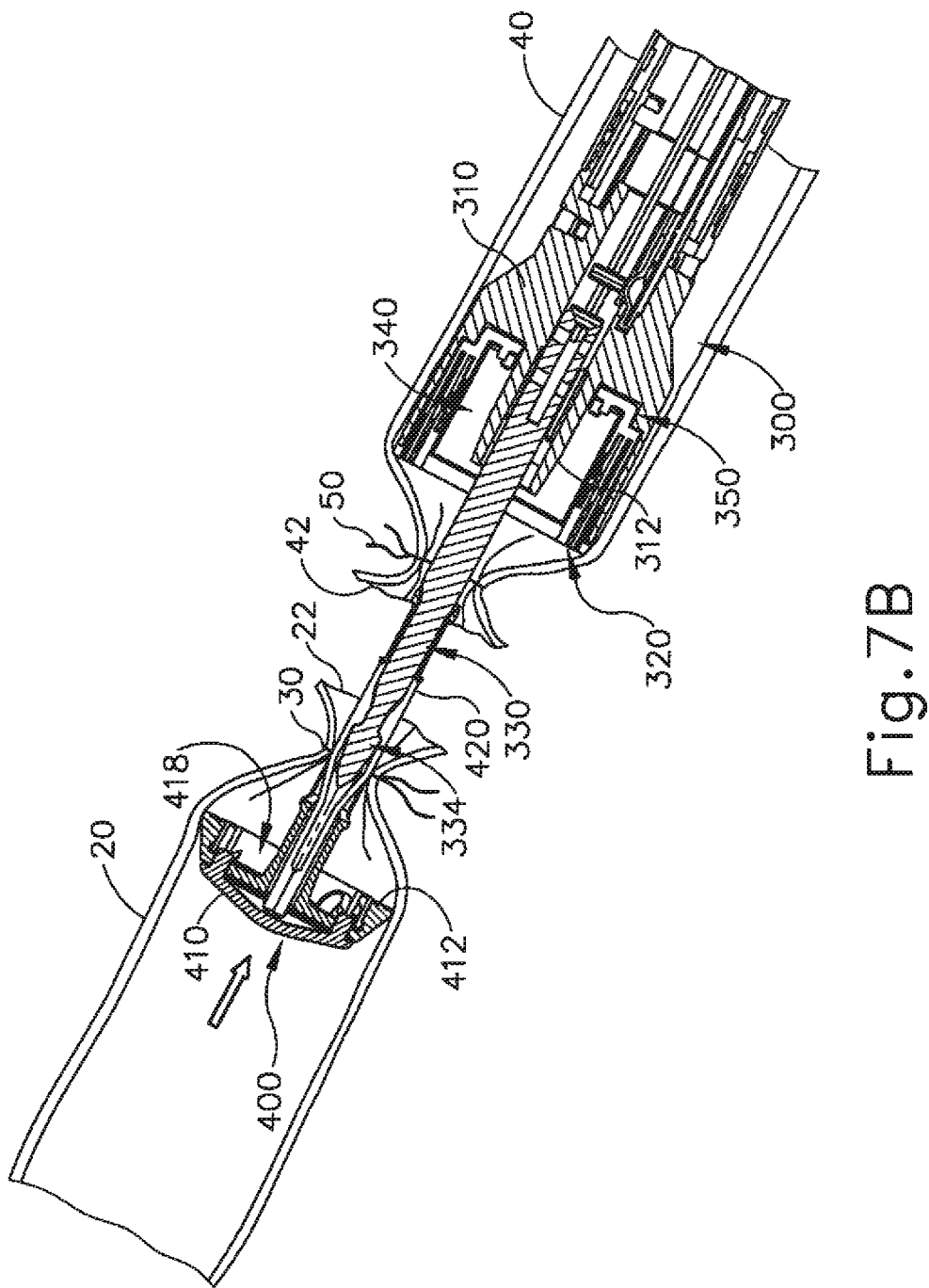
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
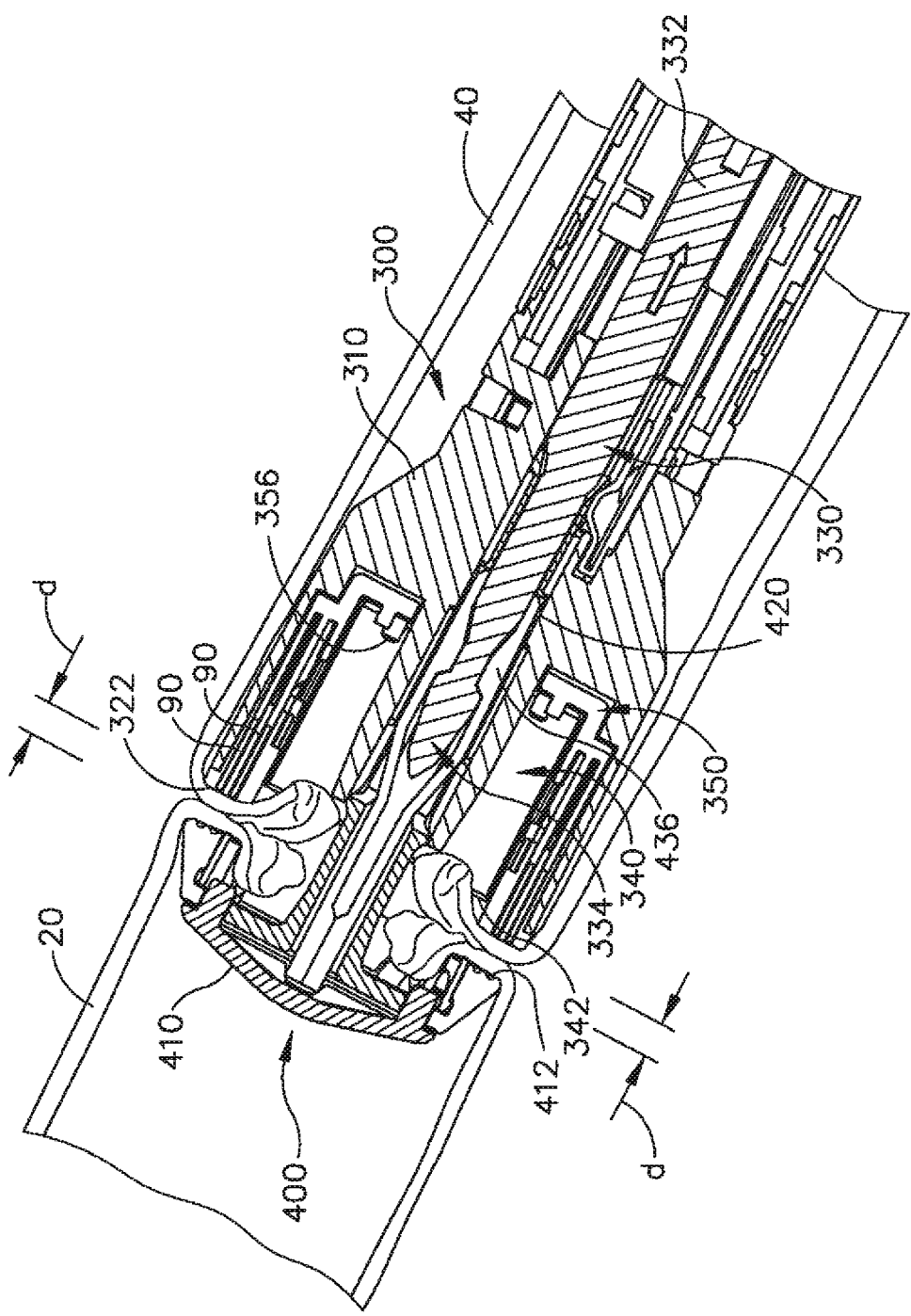
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding handle assembly (100) stationary via pistol grip (112). This rotation of knob (130) causes trocar (330) and anvil (400) to retract proximally, as described above. As shown in FIG. 7C, this proximal retraction of trocar (330) and anvil (400) compresses the tissue of tubular anatomical structures (20, 40) between surfaces (412, 322) of anvil (400) and stapling head assembly (300). The operator observes user feedback feature (114) to determine whether the gap distance (d) between opposing surfaces (412, 322) of anvil (400) and stapling head assembly (300) is appropriate; and makes any necessary adjustments via knob (130).

Figure 7D:
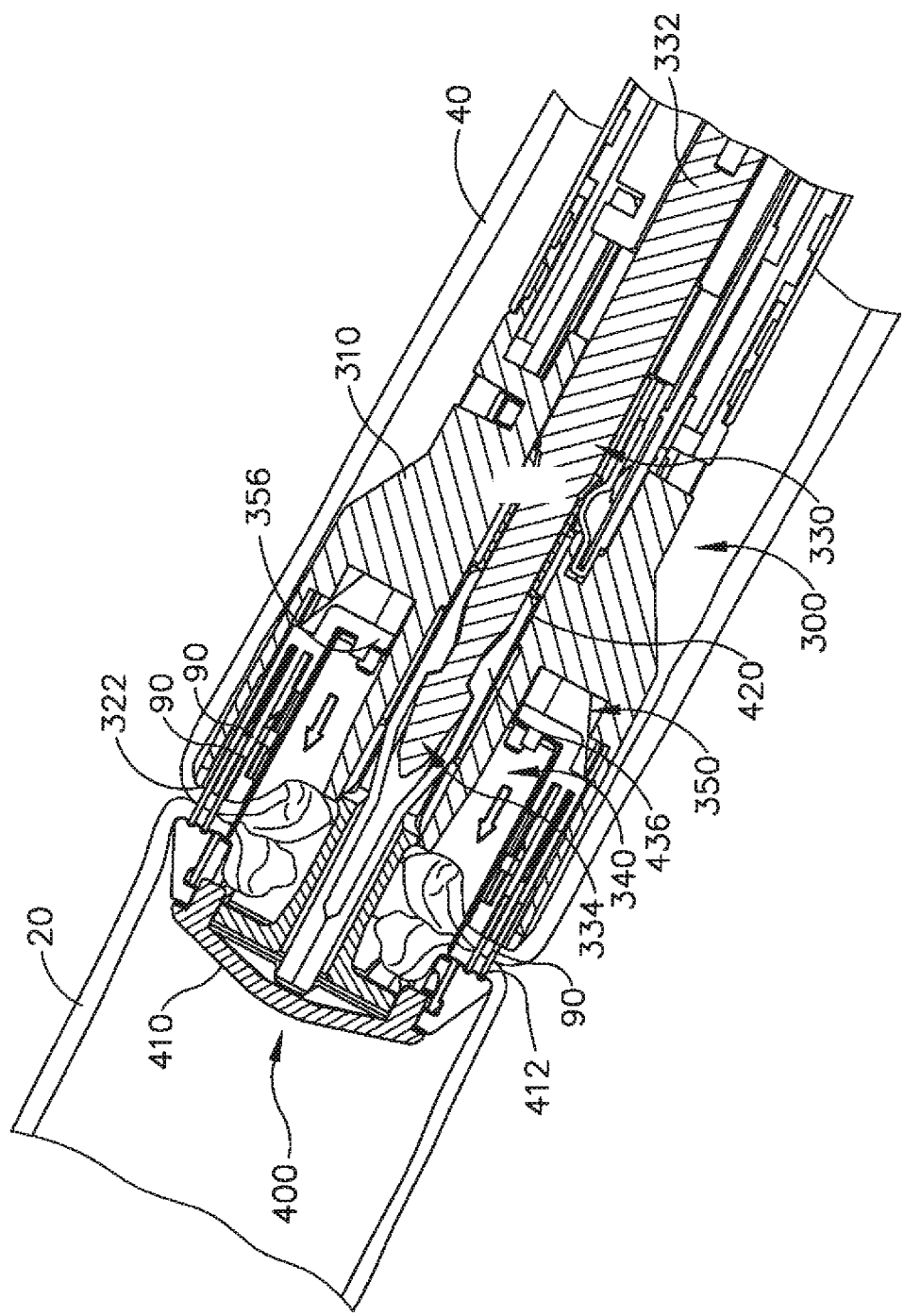
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator actuates safety trigger (140) to enable actuation of firing trigger (150). The operator then actuates firing trigger (150). This actuation of firing trigger (150) in turn actuates a switch of motor activation module (180), which in turn activates motor (160) to thereby actuate stapling head assembly (300) by driving knife member (340) and staple driver member (350) distally as shown in FIG. 7D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when knife member (340) completes a full distal range of motion from the position shown in FIG. 7C to the position shown in FIG. 7D. The drive mechanism for knife member (340) may provide an increasing mechanical advantage as knife member (340) reaches the end of its distal movement, thereby providing greater force by which to break washer (417). Of course, breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and cutting edge (342).

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together, thereby coupling tubular anatomical structure (20) with tubular anatomical structure (40).

Figure 7E:
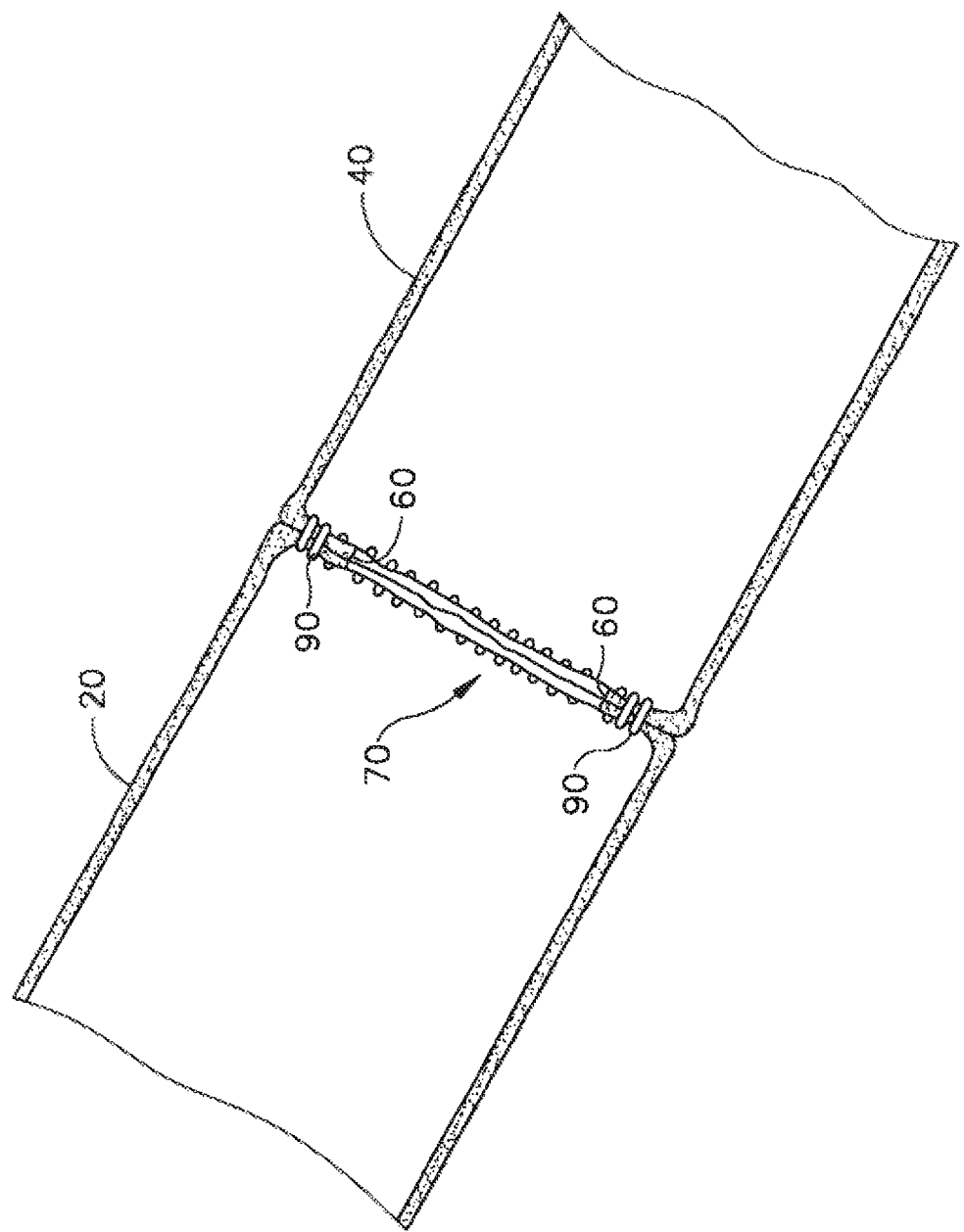
FIG. 7E depicts a cross-sectional side view of the first and second sections of the digestive tract of FIG. 7A joined together at an end-to-end anastomosis.

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

In some instances, it may be desirable to change the configuration and arrangement of staple forming pockets (414) in anvil (400). It should be understood that reconfiguring and rearranging staple forming pockets (414) may result in reconfiguration and rearrangement of staples (90) that are formed by staple forming pockets (414). For instance, the configuration and arrangement of staple forming pockets (414) may affect the structural integrity of an anastomosis (70) that is secured by staples (90). In addition, the configuration and arrangement of staple forming pockets (414) may affect the hemostasis that is achieved at an anastomosis (70) that is secured by staples (90).

D. Exemplary Circular Stapling Instrument with Sensors

Figure 8A:
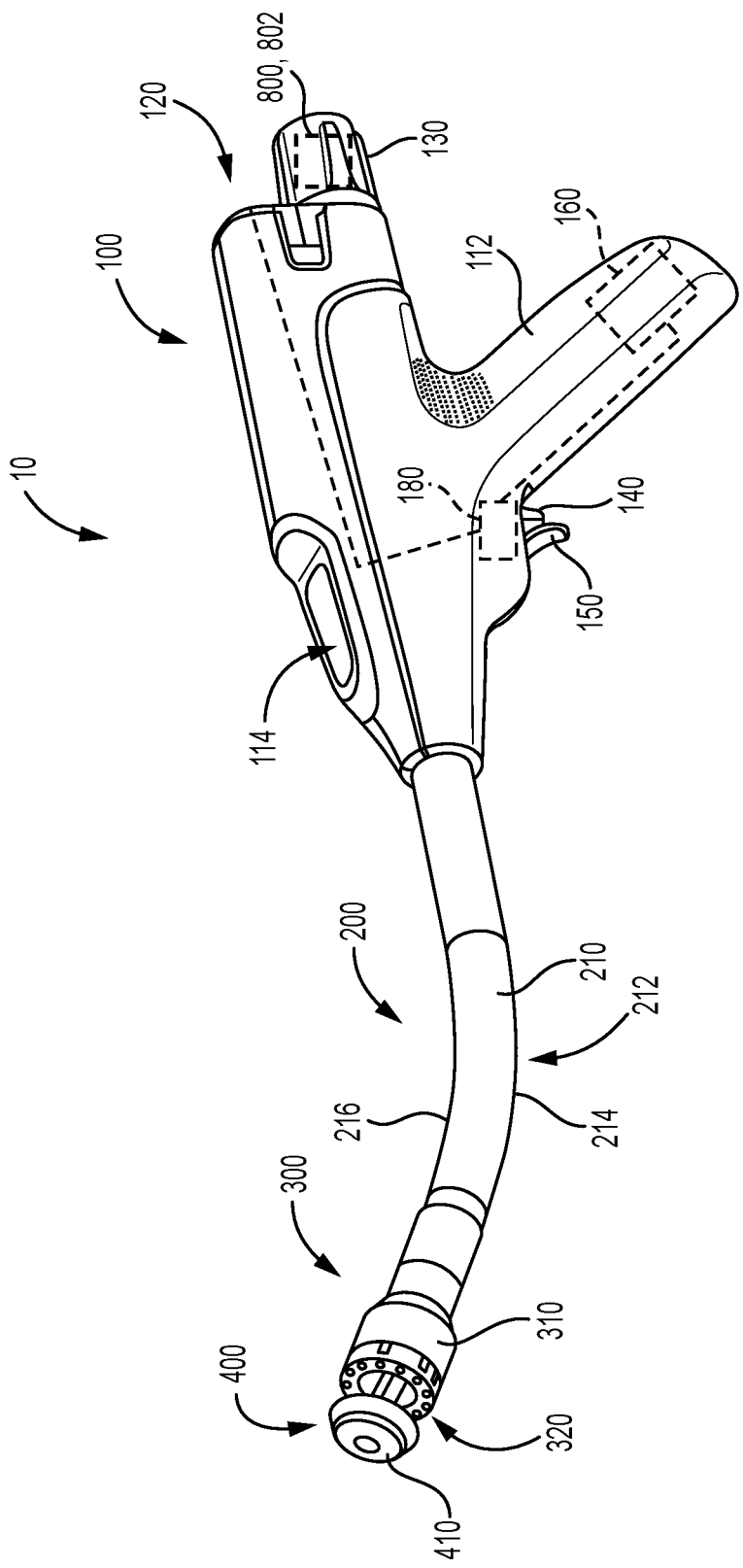
FIG. 8A depicts a circular stapler including sensors configured to generate data associated with the device operation or tissue status that can be used to determine trocar position and anvil state, according to one aspect of the present disclosure.

Circular stapler (10) described herein can include components, such as sensors (800, 802) shown in FIG. 8A, that generate and communicate data associated with operation of the circular stapler (10) or tissue status that can be utilized to determine trocar position for circular stapler (10). The term tissue status can relate to tissue compression, but is not limited thereto and can apply to any detectable condition regarding the tissue. The trocar position can also be used to determine an anvil state when anvil (400) is attached to the trocar (330), as described herein, although in other examples, when the anvil (400) is not attached to the trocar (330), the sensors (800, 802) can be utilized to determine the position of the trocar (330). The anvil state is determined based on the position or movement of anvil (400) with respect to stapling head assembly (300) as a result of translation of trocar (330), as described in further detail in the examples herein. For example, the anvil state can be based on the gap between the anvil surface (412) and the staple deck surface (322) of circular stapler (10).

The generated data can be used, as described in the examples set forth herein, to determine when the proper number of rotations of knob (130) for removal of circular stapler (10) are completed, to minimize tissue and anastomosis damage during removal. In another example, the generated data can be used to alert the user of unintentional motion of trocar (330), i.e., movement or change in position of trocar (330) that is not associated with user operation of knob (130). In yet another example, the generated data can be used to establish a home position for trocar (330) after installation of handle battery (122) to allow further tracking of the position of trocar (330). In a further example, the generated data can be used to determine a fully closed anvil state based on trocar position to determine a start condition prior to initiating a firing of circular stapler (10).

Figure 9:
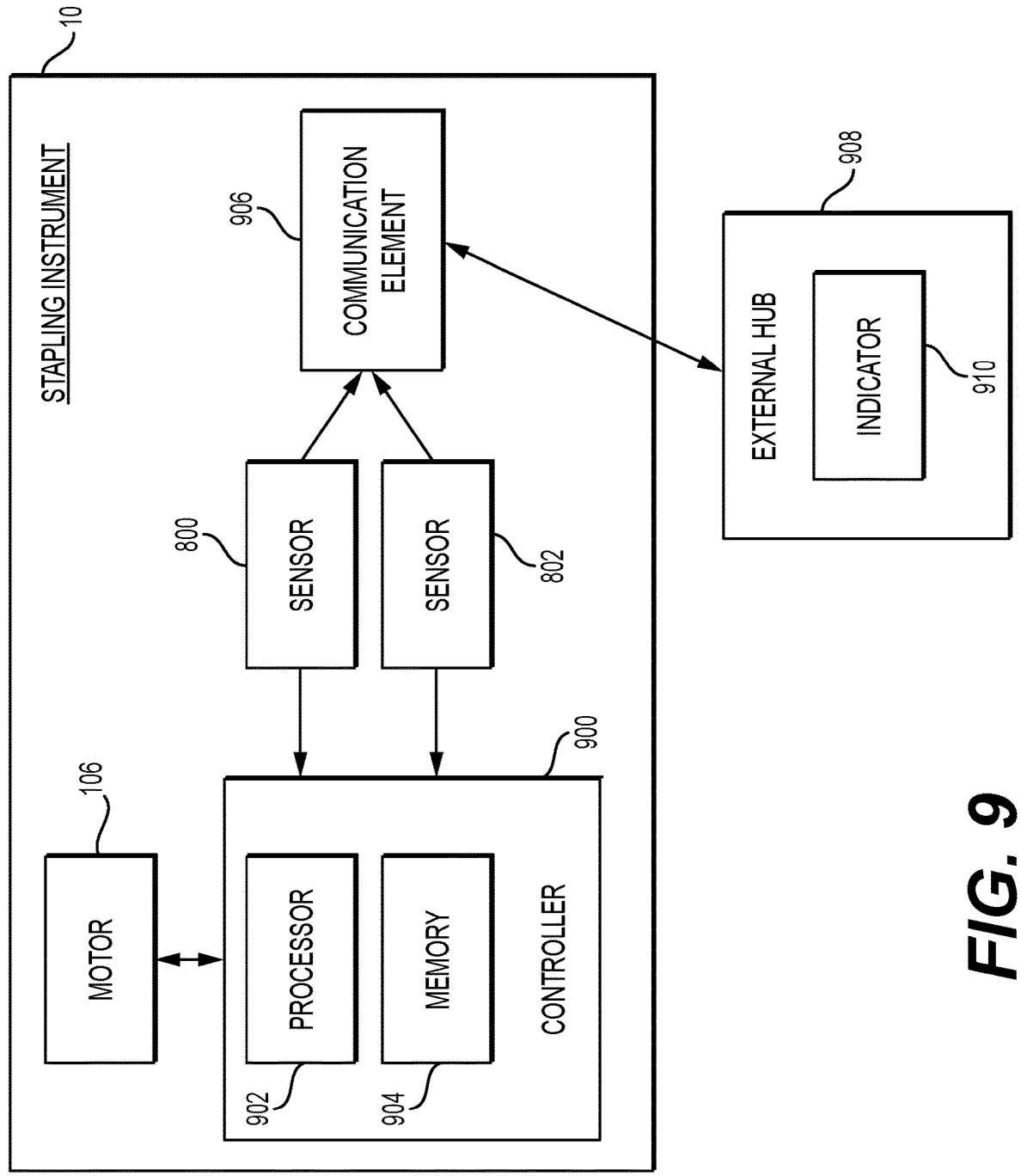
FIG. 9 is a component diagram of an example circular stapler, according to one aspect of the present disclosure.

Although exemplary uses for the generated data are described, it is to be understood that the generated data can be used to determine other types and/or numbers of anvil states based on the position of the trocar in other examples. In one example, the data associated with the trocar position and/or the associated anvil state is communicated to external hub (908), as shown in FIG. 9, to provide indicator (910) associated with the trocar position and/or the anvil state. Indicator (910) can provide feedback directly to the user of the circular stapler (10) and/or to staff located within the operating room. Indicator (910) can provide any number and/or types of feedback that can be provided in various combinations, such as a visual indicator provided on an onscreen display or an audible or tactile indicator, by way of example only. Indicator (910) can be used, for example, to provide feedback regarding the trocar position and/or the anvil state, based on position of trocar (330) (with or without the anvil (400) attached), without relying on visualization by the user of circular stapler (10) itself during operation. In another example, controller (900) (as shown in FIG. 9) receives data from sensors (800, 802) and is configured to determine the trocar position and/or the associated anvil state based on the received data.

Figure 10A:
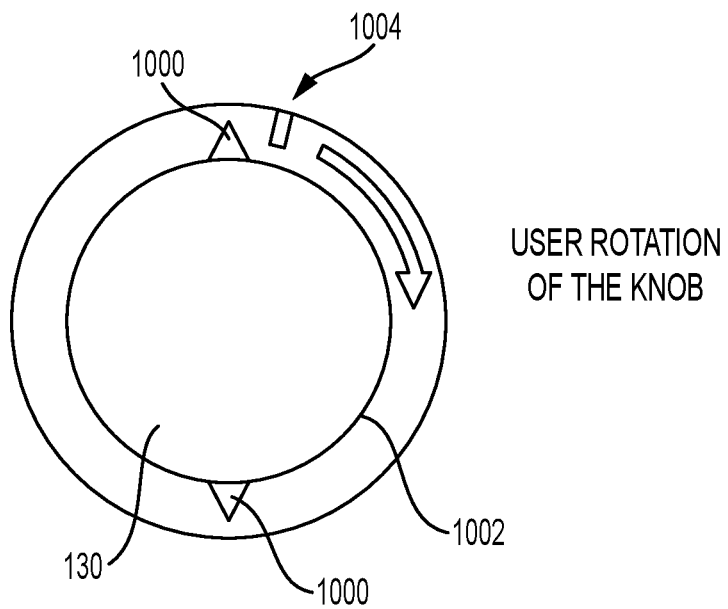
FIG. 10A depicts a knob that includes protrusions, for generating increased magnitude torque values used to determine trocar position and anvil state, in a first position, according to one aspect of the present disclosure.
Figure 10B:
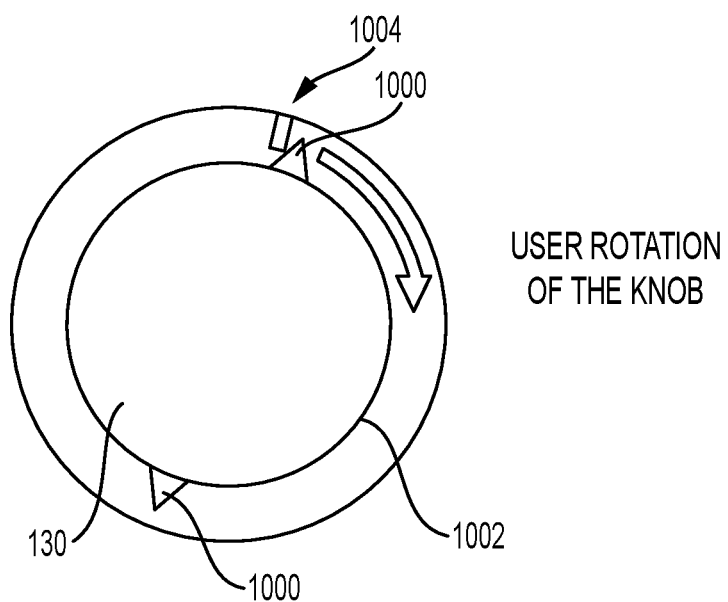
FIG. 10B depicts the knob shown in FIG. 10A in a second position, according to one aspect of the present disclosure.

Referring now to FIG. 8A, the example depicts circular stapler (10) that includes sensors (800, 802) configured to generate data associated with the trocar position. Although two sensors (800, 802) are shown in the example in FIG. 8A, other numbers and/or types of sensors can be included in circular stapler (10). In one example, at least one of sensors (800, 802) is a torque sensor configured to measure torque applied to the knob (130), such as a torque transducer, although in other examples a linear force sensor could be employed. Circular stapler (10) can include elements associated with knob (130) that provide increased magnitude torque values during rotation of knob (130), such as protrusions (1000) located on the rotating knob (130) that interface with fixed elements (1004), which are protrusions fixedly attached to the housing of circular stapler (10), as shown in FIGS. 10A and 10B.

Alternatively, circular stapler can include protrusions (1100) and fixed element (1104) that are associated with shaft assembly (200), as shown in FIG. 11A, that are configured to provide an increased magnitude torque value or increased linear force magnitude value based on linear motion of trocar (330) caused by rotation of knob (130). Although protrusions (1100) are illustrated and described as being associated with shaft assembly (200), it is to be understood that location elements (1100) could be associated with any other linear moving element of circular stapler (10) based on rotation of knob (130), such as a rod or screw associated with movement of trocar (330), the linear motion of which can be correlated to the position of trocar (330), or anvil (400) when attached to trocar (330). Operation of the additional elements to provide an increased load, which results in increased magnitude torque values is described in further detail below. In another example, at least one of sensors (800, 802) is a sensor configured to measure a rotational position of the knob (130), such as a rotary encoder. In the example shown in FIG. 8A, sensors (800, 802) are located within knob (130), although sensors (800, 802) can be located in an attachment to circular stapler (10), such as knob attachment (810) shown in FIG. 8B and described below.

Figure 8B:
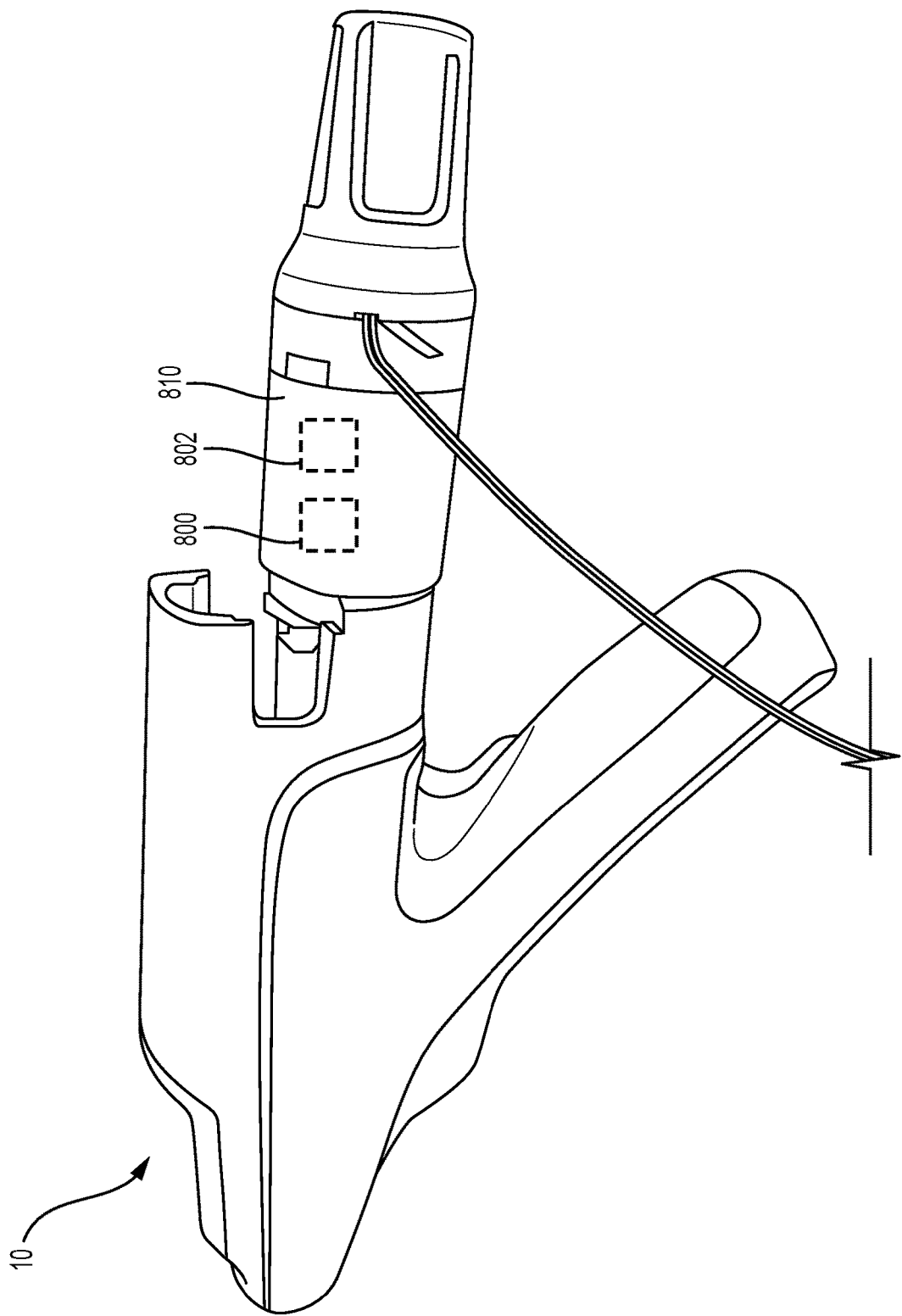
FIG. 8B depicts a circular stapler that includes a knob attachment, according to one aspect of the present disclosure.

Referring now to FIG. 8B, in another example, circular stapler (10) further includes knob attachment (810) which is configured to be coupled to knob (130). Knob attachment (810) is shaped to provide a user touchpoint that mimics the geometry of knob (130). In this example, sensors (800, 802) are located in knob attachment (810). In some examples, knob attachment (810) can also include communication element (906), as shown in FIG. 9 and described below.

FIG. 9 is a block diagram of circular stapler (10) including sensors (800, 802). In some examples, sensors (800, 802) are coupled to controller (900) of circular stapler (10). Controller (900) can include hardware and/or software to help control (i.e., generate or receive firing signals to and from stapling head assembly (300)), or monitor the device to determine anvil state (i.e., receive data from sensors (800, 802) and determine the anvil state based on the received data).

Processor (902) can include one or more of a microprocessor, microcontroller, digital signal processor, co-processor or the like or combinations thereof capable of executing stored instructions and operating upon stored data. Memory (908) can include, in some implementations, one or more suitable types of memory (e.g., such as volatile or non-volatile memory, random access memory (RAM), read only memory (ROM), programmable read-only memory (PROM), erasable programmable read-only memory (EPROM), electrically erasable programmable read-only memory (EEPROM), flash memory, and the like), for storing files including an operating system, application programs, executable instructions and data. In one embodiment, the processing techniques described herein can be implemented as a combination of executable instructions and data stored within memory (908). Memory (908) can include instructions that, when executed by processor (902), perform one or more processes consistent with the functionalities disclosed herein. Methods, systems, and articles of manufacture consistent with disclosed embodiments are not limited to separate programs or computers configured to perform dedicated tasks. For example, circular stapler (10) can include memory (908) that can include one or more programs to perform one or more functions of the disclosed embodiments.

Communication element (906) is coupled to sensors (800, 802) and is configured to provide the generated data from sensors (800, 802) to external hub (908). Communication element (906) can be compatible with any wireless communication method including one or more of: radio-frequency identification (RFID), near-field communication (NFC), Bluetooth™, low-energy Bluetooth™ (BLE), WiFi, or similar technologies.

External hub (908) can include an external computing system with a display for providing indicator (910), such as a visual display or audible alert or the like, associated with the anvil state based on the data received from sensors (800, 802). In one example, the displayed anvil state is correlated to the measured torque during rotation of knob (130) and/or rotational position of the knob (130), as described in further detail in the examples below.

E. Exemplary Determination of Trocar Position and/or Anvil State

FIGS. 10A and 10B depict one example of knob (130) that includes protrusions (1000) located on outer circumference (1002) thereof that result in temporarily increased magnitude torque values as a result of continued rotation of knob (130) as protrusions (1000) interface with fixed element (1004) used to determine trocar position and/or anvil state during operation of circular stapler (10). In this example, circular stapler (10) further includes fixed element (1004) located in the housing for knob (130) and partially in a path of protrusions (1000) as the knob (130) is rotated. Fixed element (1004) can be a spring element that retains its position partially within the path of knob (130) and creates an increase in magnitude of torque when protrusion (1000) passes fixed element (1004). For example, knob (130) can be rotated from the position shown in FIG. 10A to the position shown in FIG. 10B. Protrusion (1000) passes fixed element (1004) during rotation of knob (130) and creates an increase in magnitude of torque based on the increased force required for protrusion (1000) to pass fixed element (1004). An increased magnitude in the force response as a result of the increases in the magnitude of torque can be measured by at least one of sensors (800, 802) and can be correlated to the rotational position of knob (130), as described below with respect to FIG. 10C.

A number of turns of knob (130) can be determined based on the number increases in the force response sensed by at least one of sensors (800, 802), although the number of turns could also be determined based on rotational data from at least one of sensors (800, 802). This method advantageously allows for determining rotational position of knob (130), which can be correlated to the trocar position and/or anvil state without the need for a positional sensor, although in other examples, this method can be employed in combination with a positional sensor, such as a rotatory encoder. An open anvil state, for example, can be determined based on a threshold number of turns of knob (130) correlated to a change in trocar position after a firing of circular stapler (10).

Figure 10C:
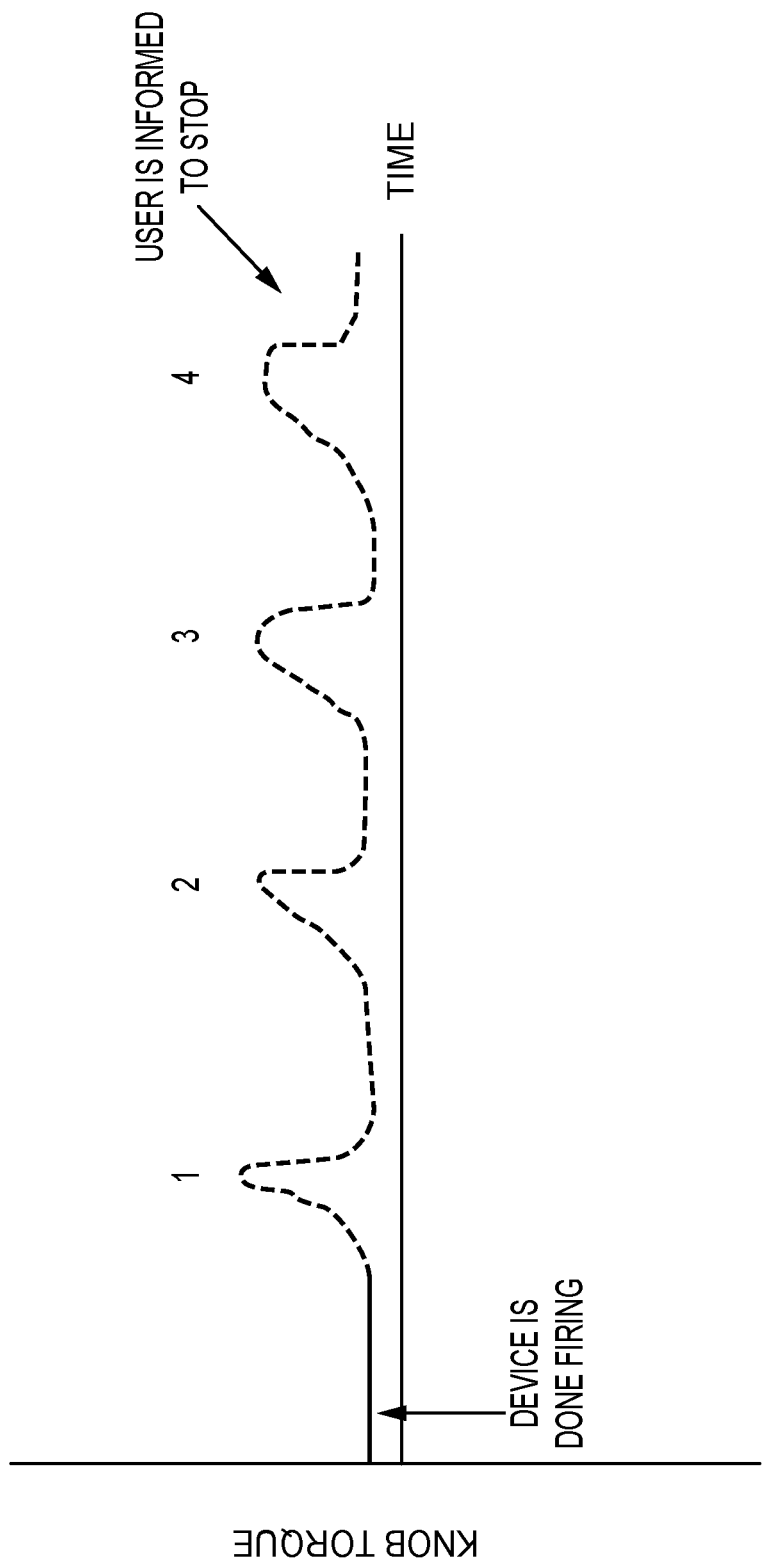
FIG. 10C is a graph of torque during rotation of the knob shown in FIGS. 10A and 10B, according to one aspect of the present disclosure.

FIG. 10C is a graph of torque on knob (130), as measured by at least one of sensors (800, 802) that provides a torque sensor, during rotation of knob (130) as shown in FIGS. 10A and 10B. Each time one of protrusions (1000) passes fixed element (1004), an increase in torque is sensed. In the depicted example, knob (130) in FIGS. 10A and 10B includes two protrusions (1000) located on diametrically opposed sides of knob (130). Each increase in magnitude of torque is therefore registered for 180 degrees of rotation of knob (130). It is to be understood that in other examples, protrusions (1000) can be located a fixed distance apart, but not diametrically opposed from one another. FIG. 10C illustrates four increases in torque corresponding to two full rotations of knob (130). In other examples, other numbers of protrusions could be located at regularly or irregularly spaced intervals about the outer circumference (1002) of knob (130) to provide a greater resolution of position of knob (130) based on the sensed increases in magnitude of torque.

The trocar position can be correlated with the number of the increases in the measured magnitude of torque during rotation of the knob (130). The trocar position can further be correlated with an anvil state when anvil (400) is attached to trocar (330). The trocar position and/or anvil state can be determined on either processor (902) of controller (900) or by one or more processors associated with external hub (908). For example, an open anvil state may be determined based on two full rotations of knob (130) (i.e., four increases in torque) after circular stapler (10) is fired, as shown in FIG. 10C, which is correlated to a change in position of the trocar. Indicator (910) of the hub (908) can provide an indication of an open anvil state, such as a visual indication or an alert, after a threshold number of increases in the measured torque after the firing of circular stapler (10) to inform the user to stop opening circular stapler (10) to minimize tissue and anastomosis damage during removal of circular stapler (10). Indicator (910) can also provide an indication to keep turning knob (130) in the event that the open anvil state has not yet been reached based on the position of the trocar.

Figure 11C:
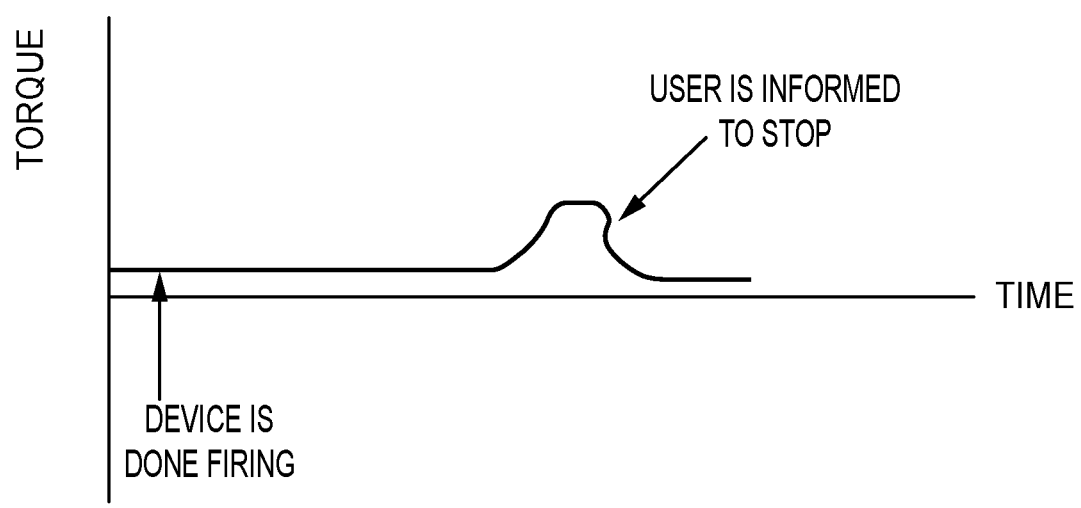
FIG. 11C is a graph of torque during rotation of the knob of the circular stapler shown in FIGS. 11A and 11B, according to one aspect of the present disclosure.

FIGS. 11A and 11B depicts one example of circular stapler (10) that includes protrusion (1100) located on surface (1102) of shaft assembly (200) thereof that can generate increases in the magnitude of linear force required to translate shaft assembly (200), which results in increased magnitude torque values used to determine trocar position and/or associated anvil state during operation of circular stapler (10). Although protrusion (1100) is illustrated and described as being associated with shaft assembly (200), it is to be understood that protrusion (1100) could be associated with any other linear moving element of circular stapler (10) that based on rotation of knob (130), the linear motion of which can be correlated to the position of trocar (330) or anvil (400) when attached to trocar (330). Although this example illustrates protrusion (1100) on surface (1102) of shaft assembly (200), protrusion (1100) could alternatively be positioned on any linearly moving element associated with trocar (330) that can be correlated to linear motion of trocar (330). In this example, circular stapler (10) further includes fixed element (1104) located in the housing for shaft assembly (200) and partially in a path of protrusion (1100) as shaft assembly (200) moves linearly based on rotation of knob (130). Fixed element (1104) can be a spring element that retains its position partially within the path of shaft assembly (200) and creates an increase in magnitude of torque when protrusion (1100) passes fixed element (1104). For example, knob (130) can be rotated to move shaft assembly (200) from the position shown in FIG. 11A to the position shown in FIG. 11B. Protrusion (1100) passes fixed element (1004) based on linear motion of shaft assembly (200) caused by rotation of knob (130) and creates an increase in magnitude torque value based on the increased force required for protrusion (1100) to pass fixed element (1104). The increases in magnitude of torque can be measured by at least one of sensors (800, 802) and can be correlated to the linear motion of the trocar (330) based on rotational position of knob (130), as described below with respect to FIG. 11C. This method advantageously allows for determining absolute position of trocar (330) or anvil (400) based on the known position of protrusion (1100) on the surface of shaft assembly (200), for example.

FIG. 11C is a graph of torque versus time, as measured by at least one of sensors (800, 802) that provides a torque sensor, during linear translation of shaft assembly (200) as shown in FIGS. 11A and 11B. As protrusion (1100) passes fixed element (1104), an increase in magnitude of torque is sensed. In the depicted example, shaft assembly (200) in FIGS. 11A and 11B includes a single protrusion (1100) on surface (1102). The increase in magnitude of torque is therefore registered to a known linear position of shaft assembly (200), which can be correlated to rotation and/or position of knob (130). FIG. 11C illustrates a single increase in torque magnitude corresponding to linear translation of shaft assembly (200) based on two full rotations of knob (130). In other examples, other numbers of protrusions could be located at various location on surface (1002) of shaft assembly (200) (or other linearly translating elements associated with trocar (330) and/or anvil (400) when attached) to identify other positions of trocar (330). In some examples, the position of trocar (330) can be correlated to one or more of the anvil states as described herein.

The trocar position and/or anvil state can be correlated with the increase in the measured torque during rotation of the knob (130) based on the known positions of protrusion (1100) on surface (1102) of shaft assembly (200) and fixed element (1104). The trocar position and/or anvil state can be determined on either processor (902) of controller (900) or by one or more processors associated with external hub (908). For example, protrusion (1100) and fixed element (1104) can be positioned to identify an open anvil state based on the increase in magnitude torque after circular stapler (10) is fired, as shown in FIG. 11C (i.e., linear motion of shaft assembly (200) from the firing position is sufficient to indicate two full rotations of knob (130)). Indicator (910) of the hub (908) can provide an indication of an open anvil state, such as a visual indication or an alert, after a threshold number of increases in the measured magnitude of torque after the firing of circular stapler (10) to inform the user to stop opening circular stapler (10) to minimize tissue and anastomosis damage during removal of circular stapler (10).

Figure 22:
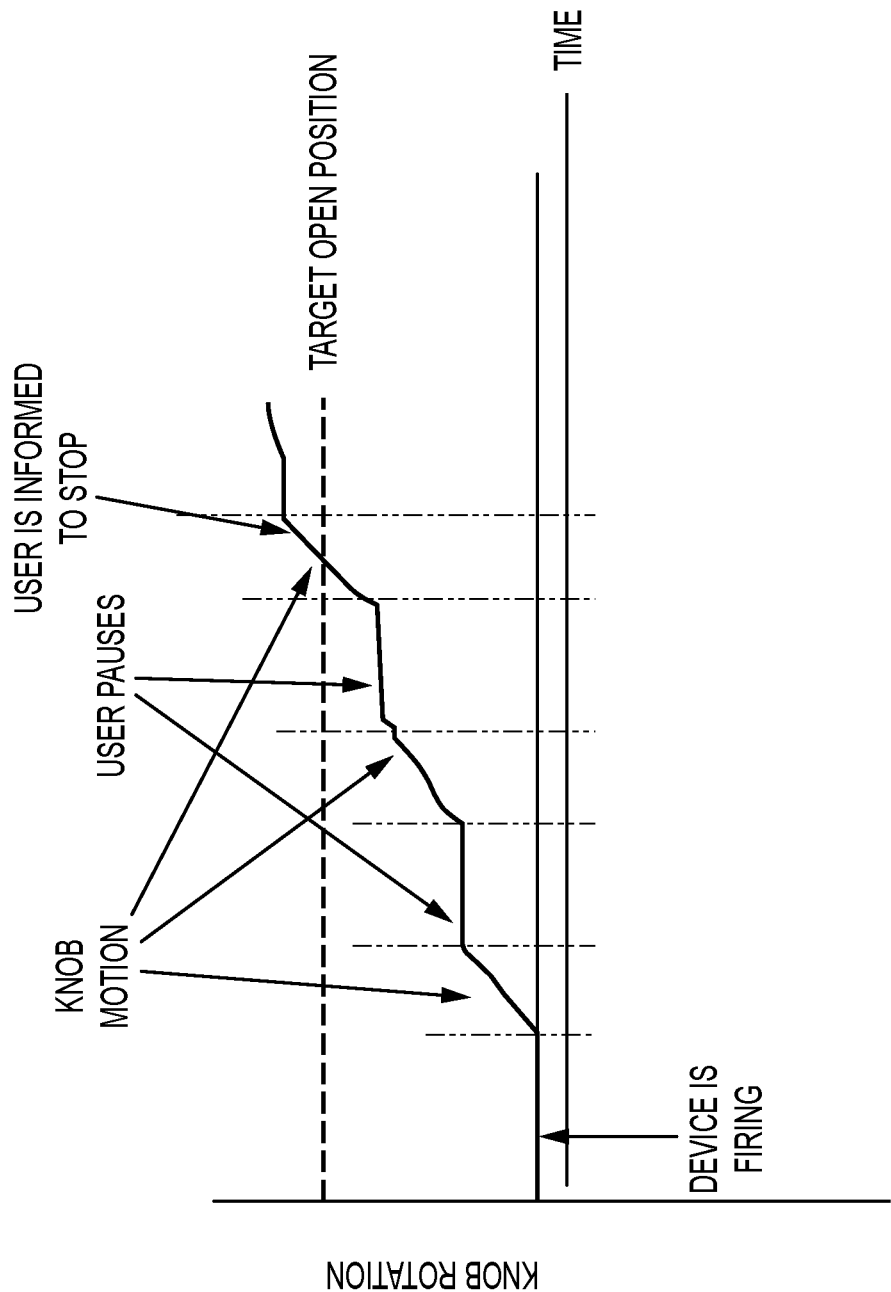
FIG. 22 depicts a graph of knob rotation versus time during opening of the circular stapler shown in FIG. 8A after firing, according to one aspect of the present disclosure.

In another example, an open anvil state (as associated with trocar position) can be determined based on data generated by at least one of sensors (800, 802) which is a rotary encoder, although other rotational position sensors could be employed. FIG. 22 depicts a graph of rotation of knob (130) as measured by at least one of sensors (800, 802) versus time. While circular stapler (10) is firing, knob (130) remains stationary. The rotational position of knob (130) during firing is recorded as a zero position. At least one of sensors (800, 802) then measures the change in rotation of knob (130) as the user operates knob (130) to open the device. The data generated by sensors (800, 802) can be monitored until the rotation of knob (130) reaches a target rotation threshold (e.g., two rotations of knob (130)). The user is then notified to stop rotating knob (130).

Figure 23:
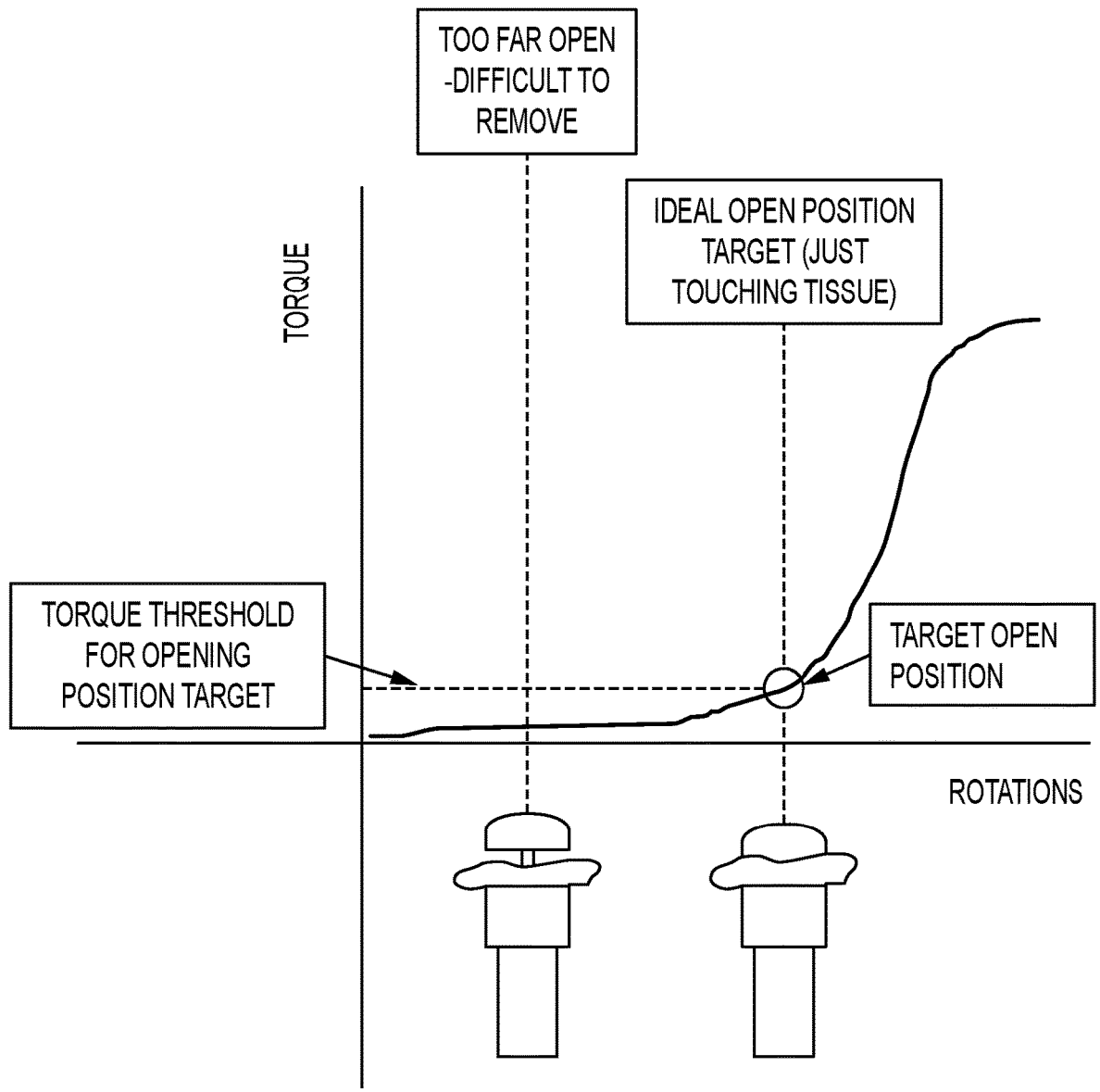
FIG. 23 depicts a graph of knob torque versus knob position during initial closing used to identify a target open position for removal (after the firing has completed), according to one aspect of the present disclosure.

In another example, sensors (800, 802) can be utilized to monitor torque versus rotation during initial closing on the tissue to determine a target or threshold open position post firing (i.e., a target tissue compression for the uncompressed tissue thickness). For example, as shown in FIG. 23, a torque fixed threshold could be used. When the torque measured by sensor (800, 802) exceeds the threshold, the position is tagged and saved to provide the target open position. Other metrics could be employed such as percentage of the maximum torque, a fixed offset from the maximum torque, a rotation offset from the maximum torque, or a rotation offset from a torque threshold value, although other metrics could be employed.

Sensors (800, 802) can provide data to controller (900) or to external hub (908) via communication element (906). The status of rotation of knob (130) can be provided as indicator (910) on external hub (908) as described below.

F. Exemplary Indication of Trocar Position and/or Anvil State

As described above, circular stapler (10) utilizes sensors (800, 802), such as a torque sensor and rotational sensor, to generate data to determine a trocar position and/or an anvil state during operation. Communication element (906) can provide the generated data to external hub (908) to provide an indicator (910) related to the trocar position and/or anvil state, such as a visual display or an audio alert, although in other examples sensors (800, 802) can provide generated data to controller (900) as described herein.

Figure 12:
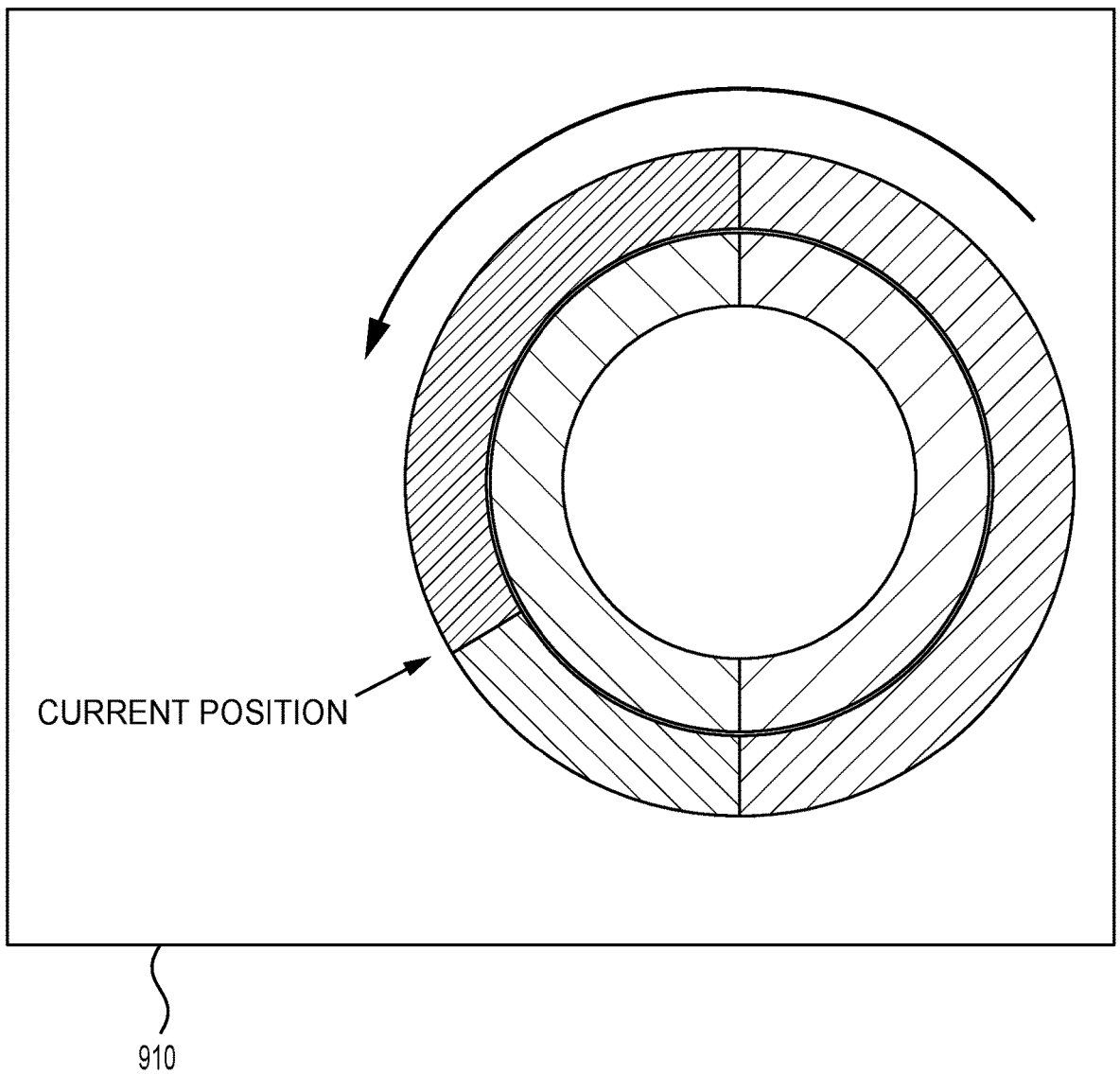
FIG. 12 depicts a visual display indicator for displaying trocar position and anvil state, according to one aspect of the present disclosure.

FIG. 12 depicts an example of a visual display on indicator (910) that can be used to move circular stapler (10) to an open anvil state after a firing of the device using two full rotations of knob (130), although other visual or audio indications can be applied for other operations of circular stapler (10). Although the visual display is related to an open anvil state, in other examples, visual displays related to trocar position when anvil (400) is not attached can be provided. In this example, visual indicator (910) includes a pair of concentric circles that represent the two full rotations of knob (130) necessary to move to the anvil open state. The indicator (910) can also provide instructions to the user, post firing of the circular stapler (10), to turn knob (130) two full rotations. Indicator (910) displays a current position of knob (130) in real-time during rotation to ensure that the proper number of rotations of knob (130) to move to the anvil open state. In one example, the circles are shaded as knob (130) is rotated to show the process. As shown in FIG. 12, the circles can be segmented to provide a more refined visual indicator of the progress.

Figure 13:
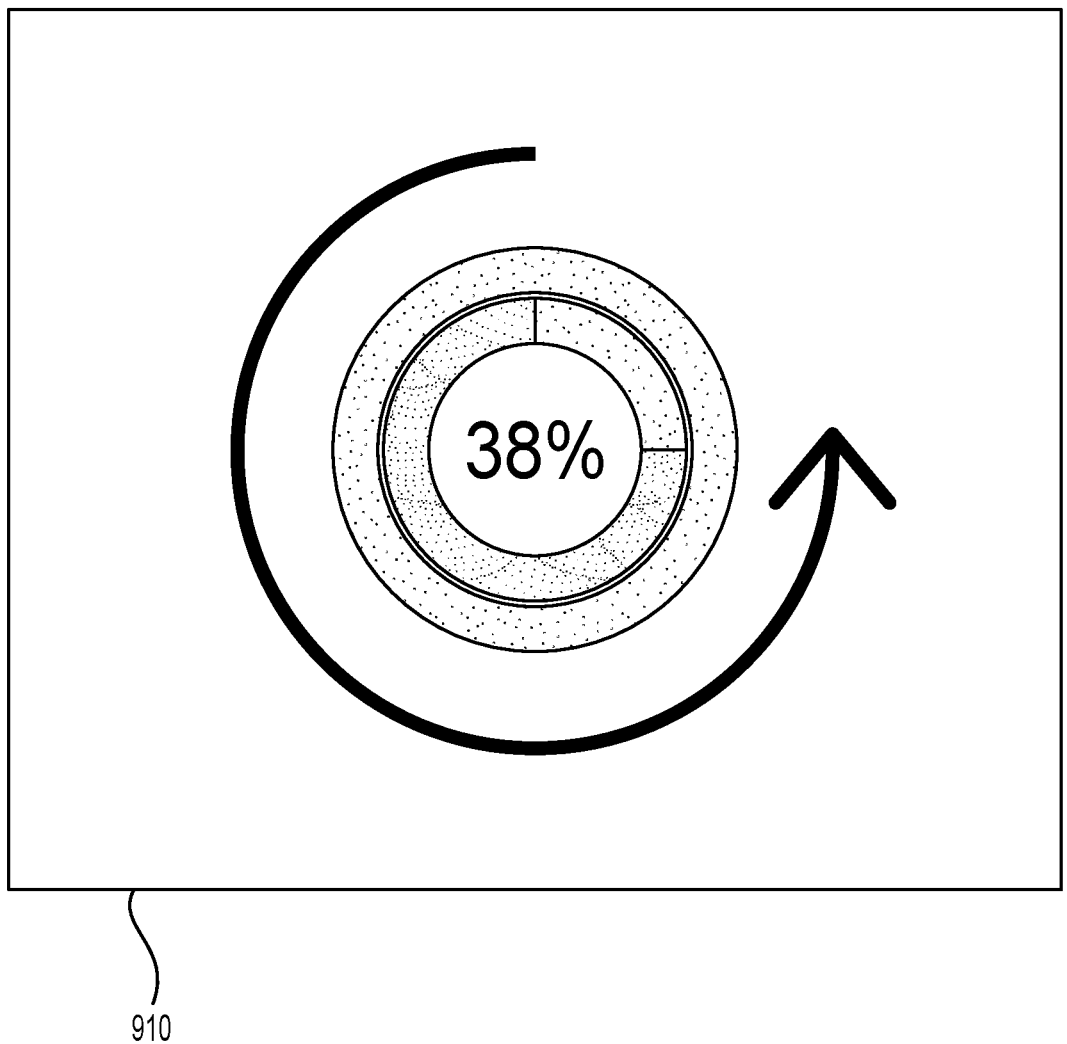
FIG. 13 depicts another visual display indicator for displaying trocar position and anvil state, according to one aspect of the present disclosure.

In another example, as depicted in FIG. 13, the progress can be depicted numerically, based on the change in position of trocar (330), although other methods can be used to provide a visual indication of progress on indicator (910), such as a graphical progress indicator. In any of the examples described, once knob (130) is fully rotated two times to provide the anvil open state, indicator (910) can provide a user prompt to remove the tool, such as a visual or auditory prompt. In other examples, indicator (910) can provide a two-dimensional representation of circular stapler (10) that displays rotation of knob (130) in real-time as a visual rendering.

G. Exemplary Determination of Home Anvil State

To accurately determine the position of trocar (330) related to the anvil state during operation of circular stapler (10), in some examples a home anvil state is determined prior to operation when anvil (400) is coupled to trocar (330). The home anvil state provides a reference that can be used to ensure proper trocar extension and retraction during use. The home anvil state can be determined after installation of handle battery (122). In one example, after handle battery (122) is installed, user can be prompted, such as through indicator (910), to open or close circular stapler by rotating knob (130). The user then rotates knob (130) until a hard stop is reached in either direction. Sensors (800, 802) can generate data that can be utilized by controller (900) or external hub (908) to determine the home anvil state, as described below.

Figure 14:
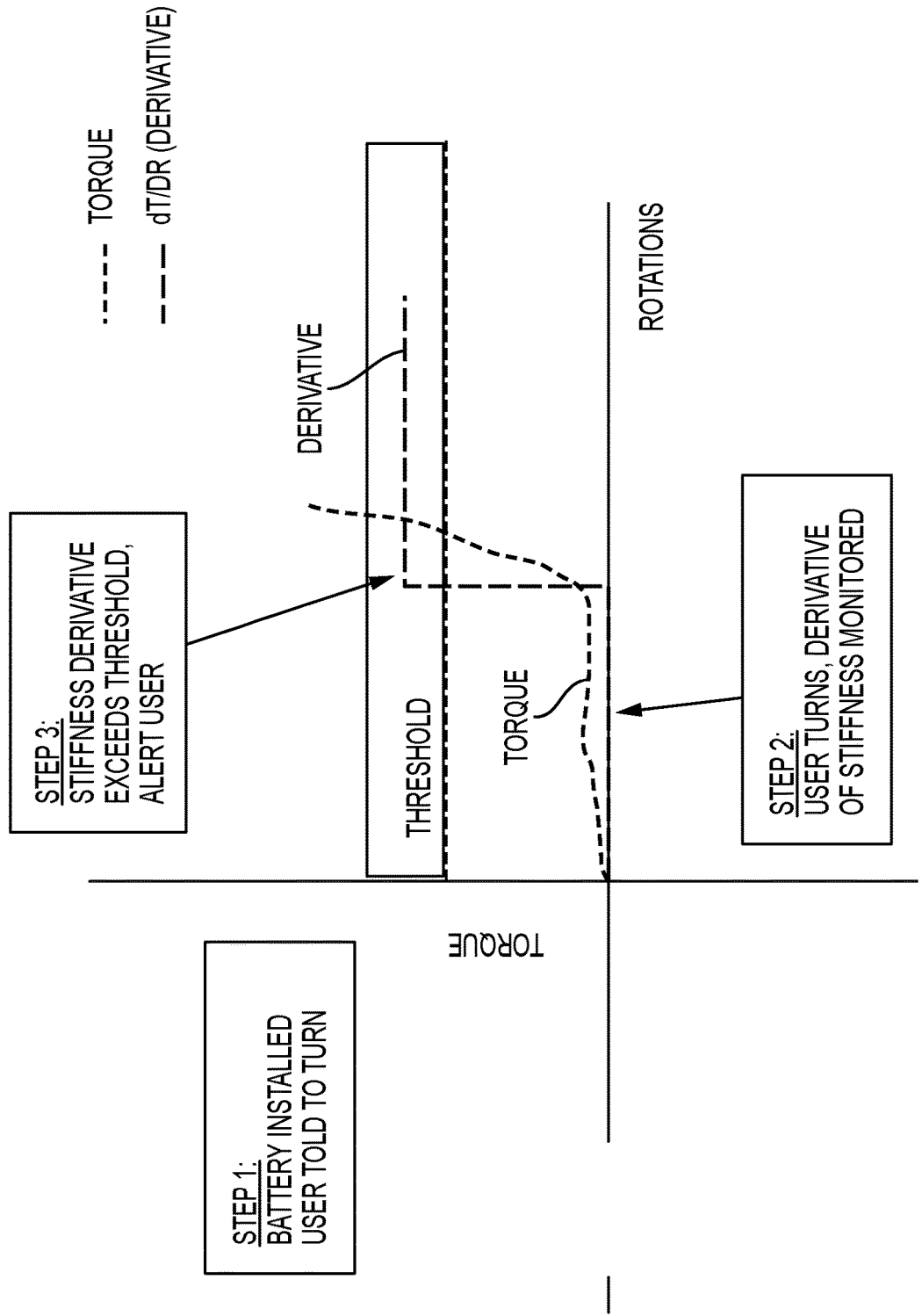
FIG. 14 depicts a graph of torque and stiffness versus knob rotations for determining a home anvil state, according to one aspect of the present disclosure.

In one example, at least one of sensors (800, 802) is a torque sensor and the home anvil state is based on a threshold increase in the measured torque as a result of the mechanical hard stop reached when opening or closing circular stapler (10). In another example, sensors (800, 802) can measure both torque and rotation of knob (130) to provide a stiffness curve of torque versus rotation as shown in FIG. 14. In this example, the stiffness curve (rotational stiffness based on change in torque and the change in rotational position) is monitored after installation of handle battery (122). The derivative of stiffness is monitored for a threshold value. When the stiffness derivative exceeds the threshold value, indicating the anvil home state based on reaching the mechanical hard stop, a user alert is provided through indicator (910) on external hub (908) or through haptic feedback on circular stapler (10), although in other examples a home anvil state may be determined when the stiffness derivative is within a threshold band including upper and lower threshold values. Once the home anvil state is reached, the user can proceed with normal use of circular stapler (10). Rotation of knob (130) can then be monitored and displayed as described above.

Figure 15A:
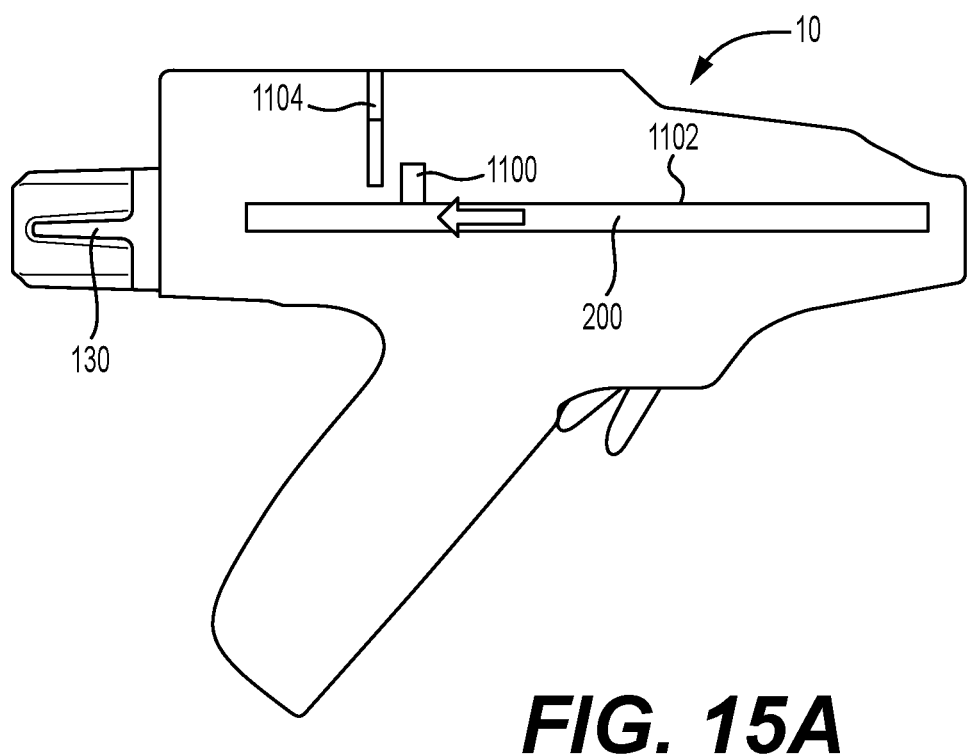
FIG. 15A depicts a circular stapler having fixed element and a protrusion for determining a home anvil state, according to one aspect of the present disclosure.

In another example, a fixed element can be located along the housing of circular stapler (10) to generate an increase in torque or stiffness to identify a home anvil state without requiring the user to fully open or close the circular stapler (10). FIG. 15A depicts circular stapler (10) having fixed element (1104) located in the housing for shaft assembly (200) and partially in a path of protrusion (1100) as the shaft assembly (200) moves linearly based on rotation of knob (130). Although this example illustrates protrusion (1100) on surface (1102) of shaft assembly (200), protrusion (1100)

could alternatively be positioned on a rod or lead screw associated with trocar (330) that can be correlated to linear motion of trocar (330). In other examples, the function of protrusion (1100) could be provided by an existing feature, such as a detent or notch on the lead screw that results in an increase in torque at a specific position. Fixed element (1104) in this example is located at a position to identify the home anvil state, although fixed element (1104) could be positioned to identify other trocar positions when anvil (400) is not attached.

Figure 15B:
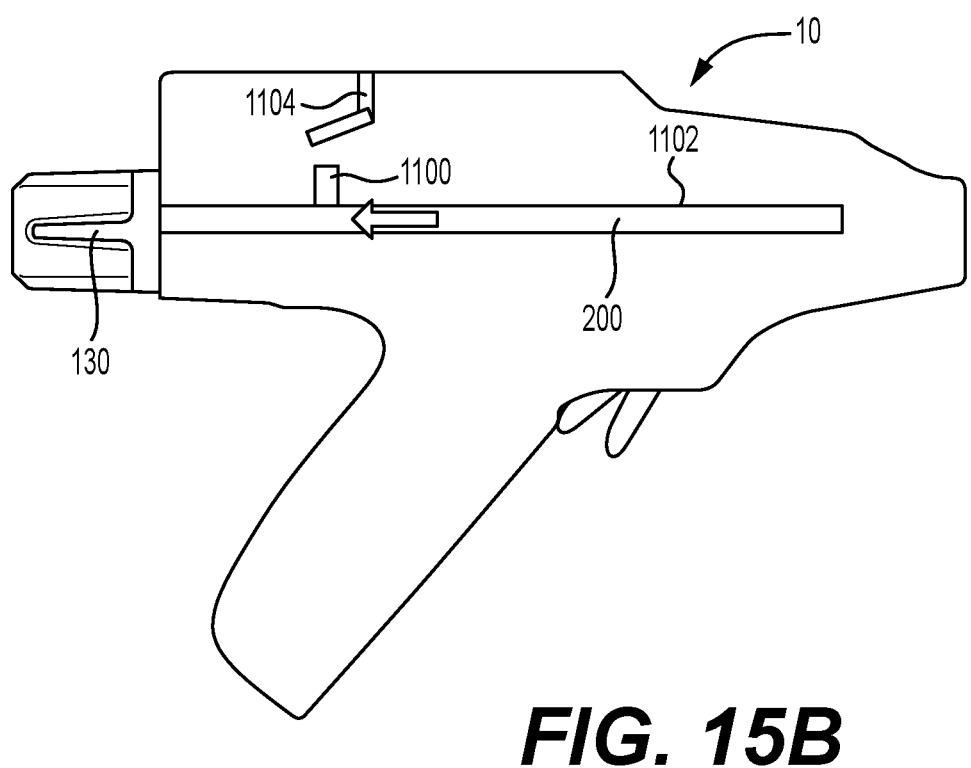
FIG. 15B depicts the circular stapler in FIG. 15A having a breakable fixed element, according to one aspect of the present disclosure.
Figure 15C:
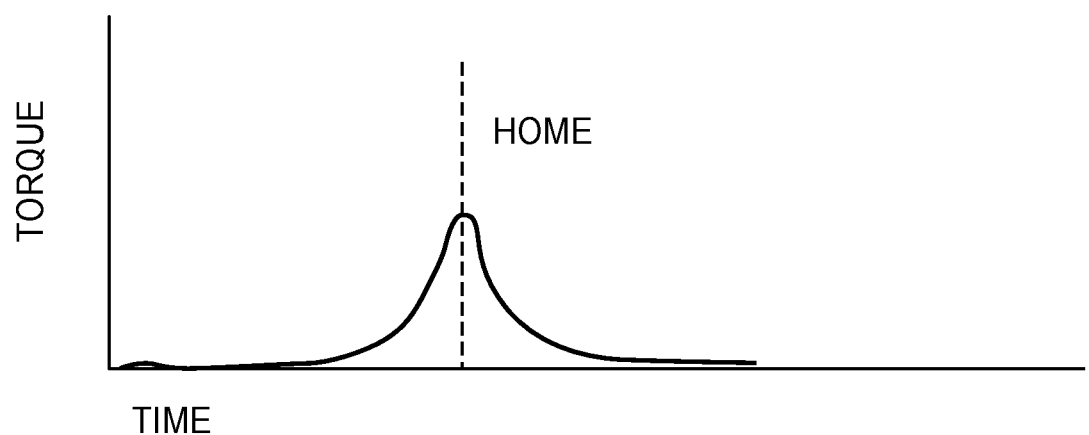
FIG. 15C depicts a graph of torque versus time during operation of the circular staplers shown in FIGS. 15A and 15B, according to one aspect of the present disclosure.

Fixed element (1104) can be a spring element that retains its position partially within the path of shaft assembly (200) and creates an increase in magnitude of torque when protrusion (1100) passes fixed element (1104). Fixed element (1104) can be formed of a plastic material, for example, such that fixed element (1104) is configured to be breakable when contacted by protrusion (1100), as shown in FIG. 15B, to provide the increase in the magnitude of torque measurement to identify the home anvil state. FIG. 15C is a graph of torque versus time, as measured by at least one of sensors (800, 802) that provides a torque sensor, during linear translation of shaft assembly (200), which is correlated to the position of trocar (330) as shown in FIGS. 15A and 15B. As protrusion (1100) passes fixed element (1104), an increase in magnitude of torque is sensed, which can be used to identify the home anvil state based on the position of fixed element (1104), although other trocar positions could be identified. In some examples, the home anvil state can be determined by a maximum torque magnitude value.

Figure 20A:
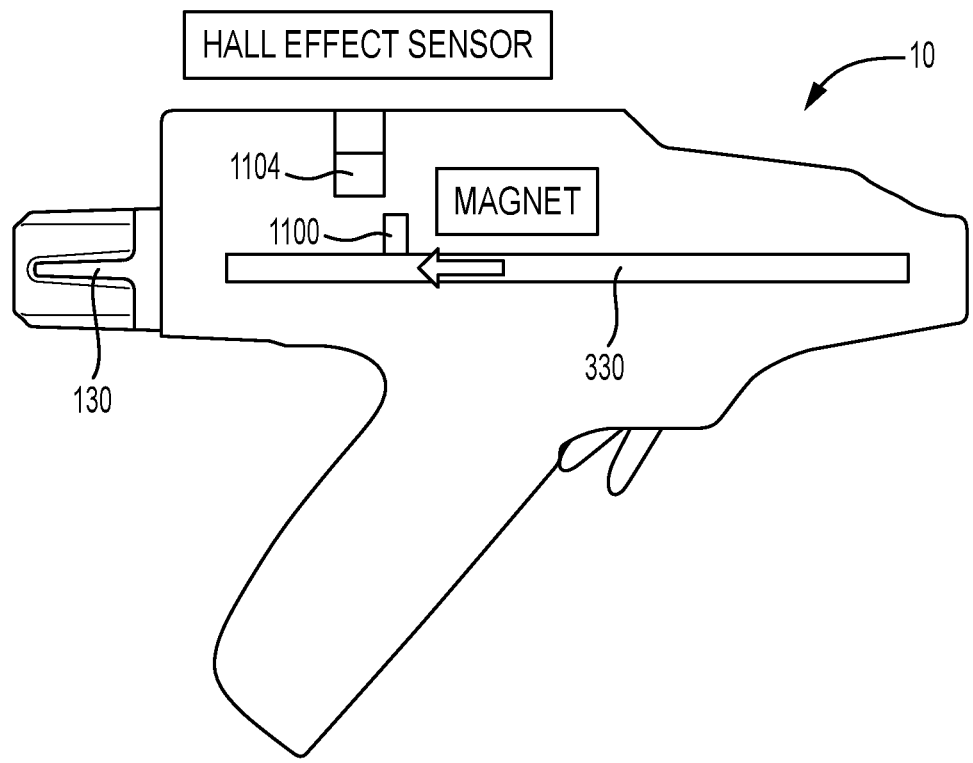
FIG. 20A depicts a circular stapler having a magnet and a hall-effect sensor for determining a home anvil state in a first position, according to one aspect of the present disclosure.
Figure 20B:
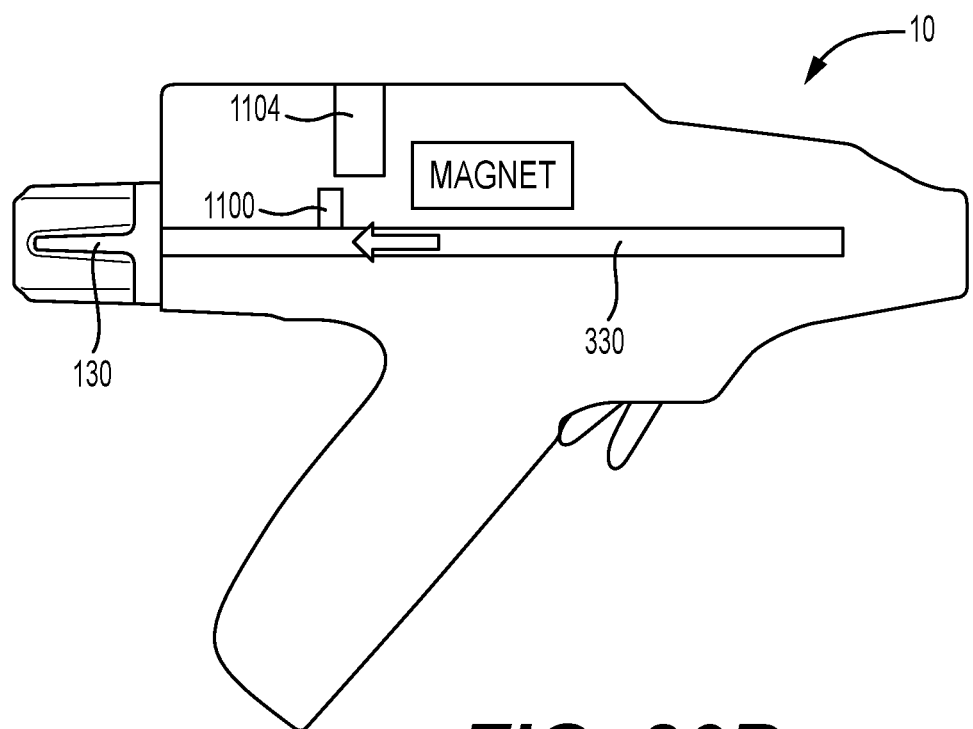
FIG. 20B depicts the circular stapler shown in FIG. 20B in a second position, according to one aspect of the present disclosure.
Figure 20C:
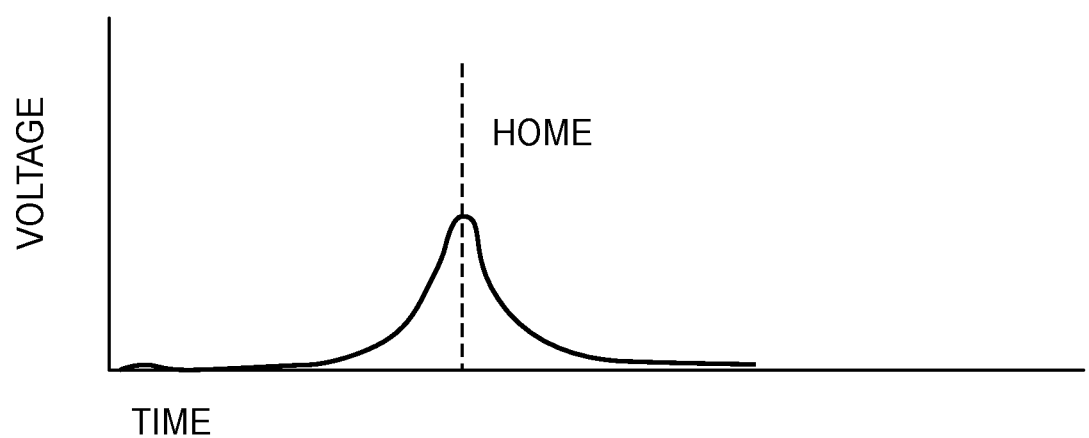
FIG. 20C depicts a graph of voltage versus time during operation of the circular stapler shown in FIGS. 20A and 20B, according to one aspect of the present disclosure.

In another example, as shown in FIGS. 20A and 20B, fixed element (1104) can be a sensor configured to produce a signal in response to the presence of moving element (2000). For example, fixed element (1104) could be a hall effect sensor and moving element (2000) could be a magnet, such that fixed element (1104) provides a extremum value in voltage (as shown in FIG. 20C) when moving element (2000), such as a magnet, goes from the position shown in FIG. 20A to the position shown in FIG. 20B and passes fixed element (1104) (e.g., hall effect sensor). The extremum voltage value can be associated with a home anvil state. In this example, moving element (2000) does not have to contact fixed element (1104). Fixed element (1104) can provide data to controller (900) or to external hub (908) via communication element (906).

In other examples, more than one fixed element (1104) can be provided at known locations in the path of moving element (2000) or protrusion (1100) to further refine detecting the home anvil state. In another example, fixed element (1104) that breaks away as shown in FIG. 15B can be combined with a mechanical hard stop when opening or closing circular stapler (10). The number of rotations of knob (130) between the increase in torque magnitude caused by fixed element (1104) and the mechanical hard stop can be measured and compared to an expected value to provide an addition check to confirm the anvil home state has been achieved. In any of the examples described above, indicator (910) can identify the home anvil state through a visual display or auditory signal.

H. Exemplary Determination of Unintentional Motion of Trocar

In another example, sensors (800, 802), such as torque and rotational sensors, of circular stapler (10) can be utilized to determine unintentional motion (i.e., motion of trocar (330) that is not caused by rotation of knob (130) by the user) during operation. For example, trocar (330) can be caused to retract when anvil (400) is being attached. The unintentional motion could potentially lead to tissue damage. Data generated by sensors (800, 802) can be used to detect unintentional motion and inform the user, such as by providing an alert, warning or other feedback to the user, through indicator (910) on external hub (908). In another example, when unintentional motion is detected, the user can receive feedback directly from circular stapler (10) initiated by controller (900), such as haptic feedback, although audio or visual alerts could also be provided.

Figure 16A:
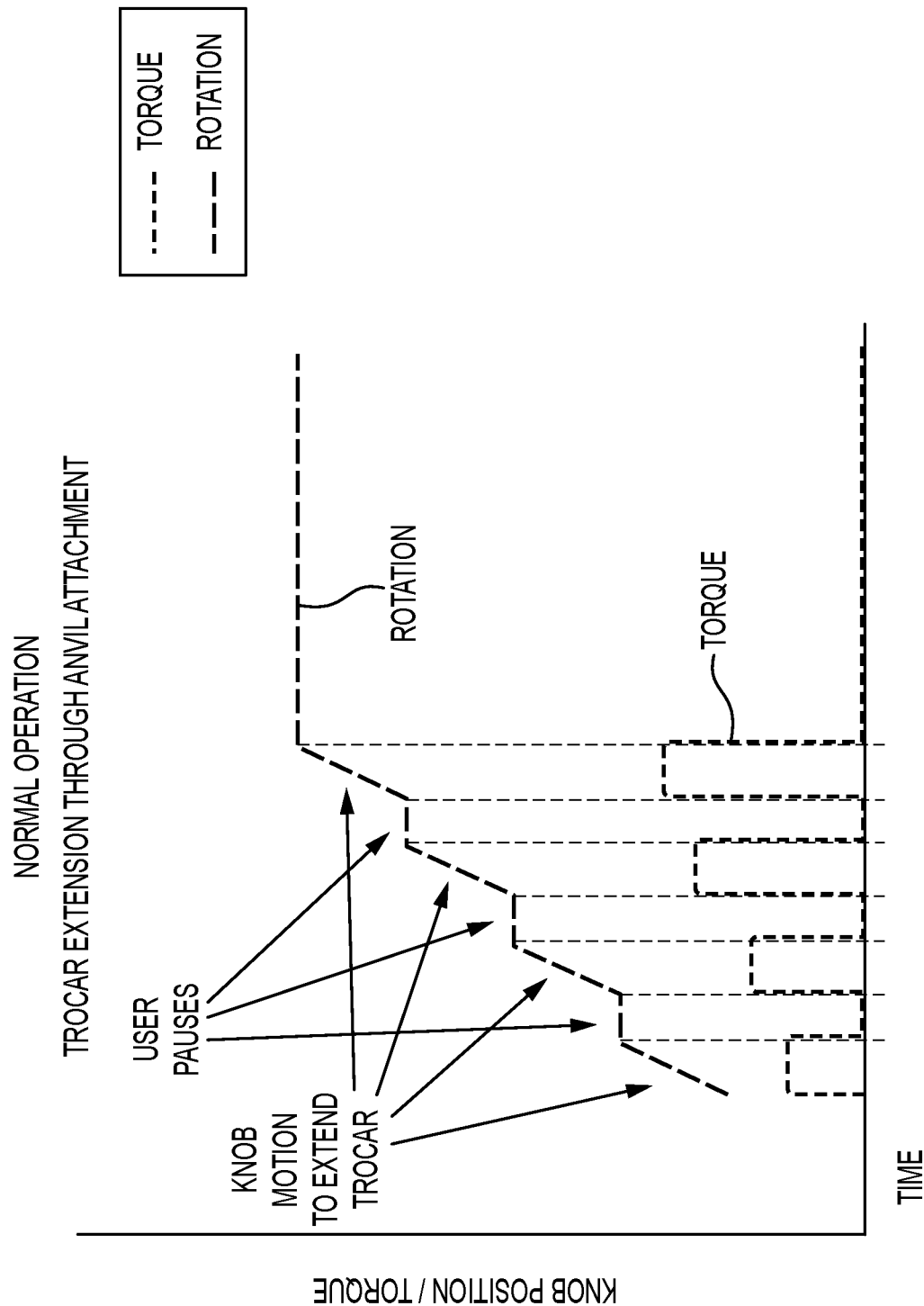
FIG. 16A depicts a graph of knob rotation and torque versus time during normal operation of the circular stapler shown in FIG. 8A, according to one aspect of the present disclosure.
Figure 16B:
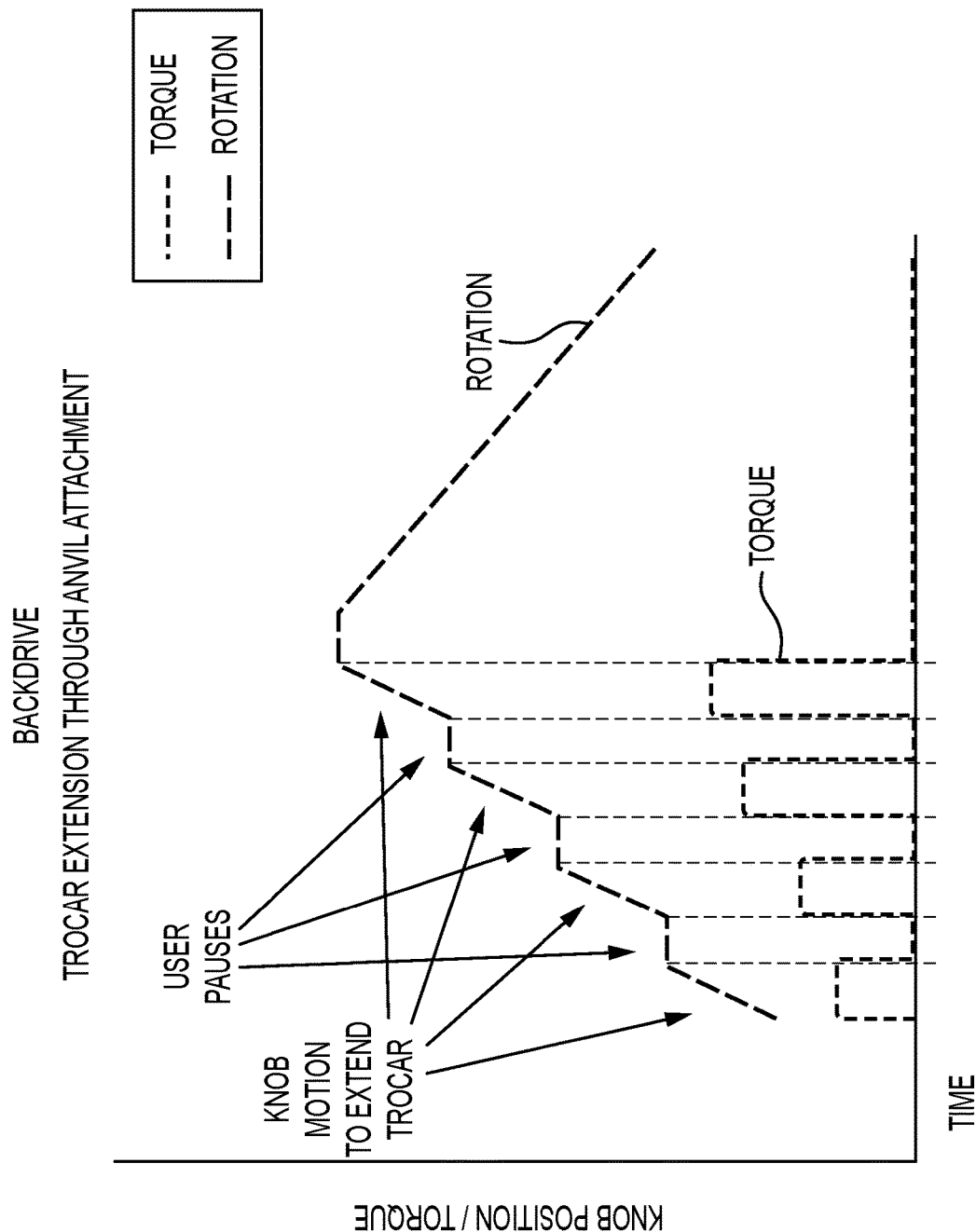
FIG. 16B depicts a graph of knob rotation and torque versus time during unintentional motion of the circular stapler shown in FIG. 8A, according to one aspect of the present disclosure.
Figure 17A:
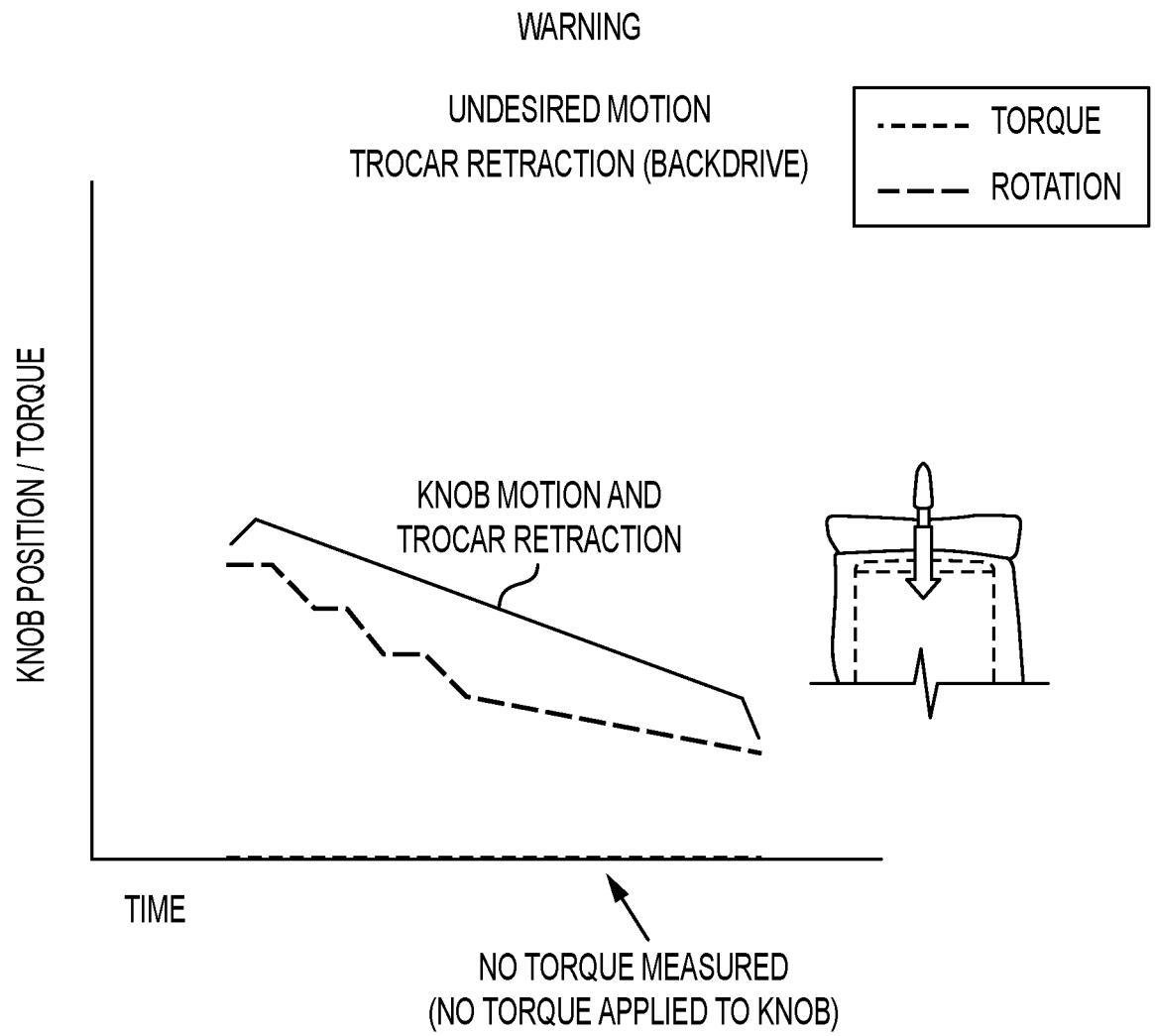
FIG. 17A depicts a graph of knob rotation and torque versus time during unintentional motion (retraction) of the circular stapler shown in FIG. 8A, according to one aspect of the present disclosure.
Figure 17B:
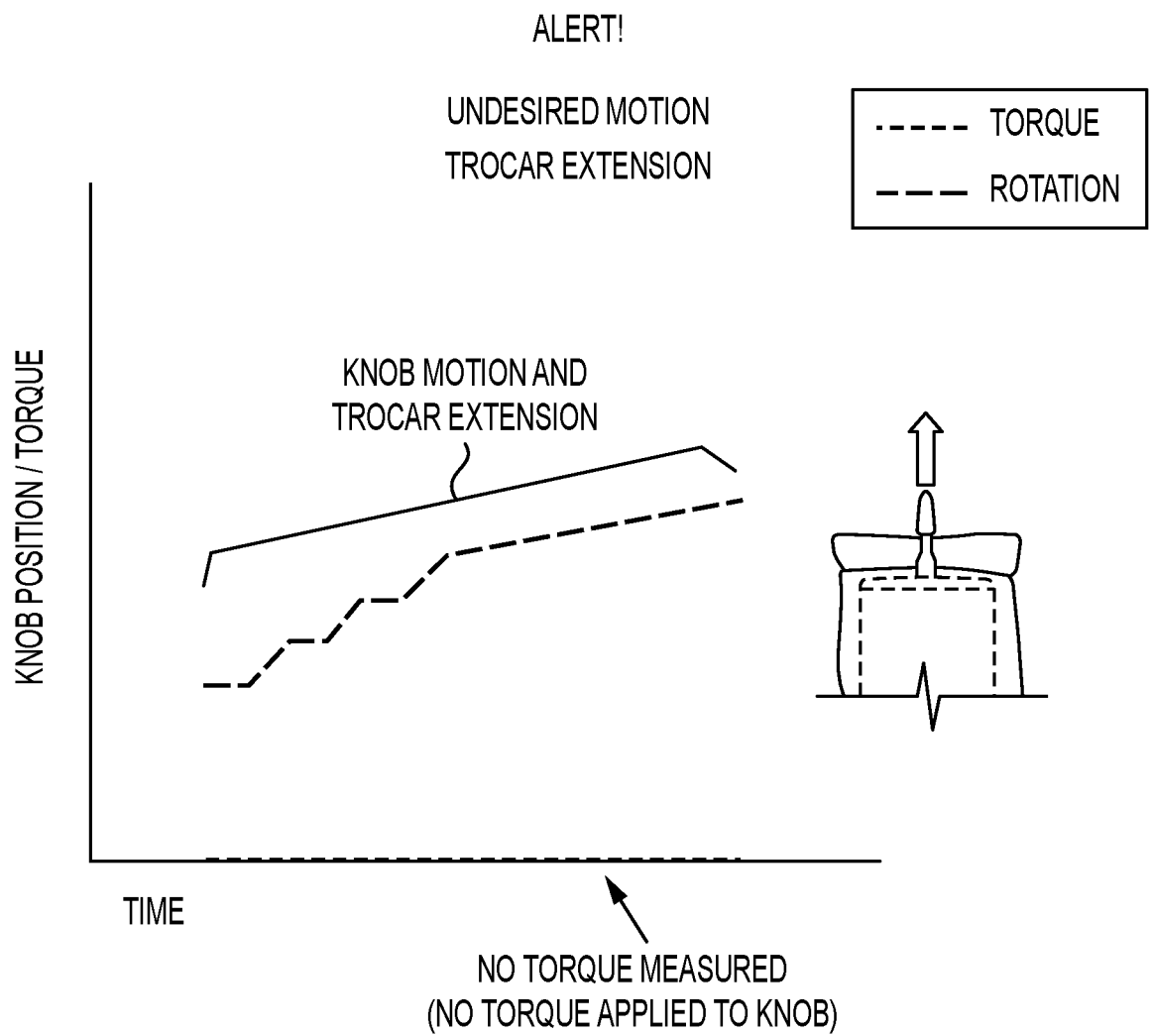
FIG. 17B depicts a graph of knob rotation and torque versus time during unintentional motion (extension) of the circular stapler shown in FIG. 8A, according to one aspect of the present disclosure.

FIG. 16A depicts a graph of rotation of knob (130) and torque sensed by sensors (800, 802) during normal operation of circular stapler (10). During normal use, user rotation of knob (130) is associated with corresponding changes in the measured magnitude of torque values or a non-zero torque (the change in the torque value can be positive or negative depending on the direction of motion). As shown in FIG. 16A, during pauses in rotation of knob (130), the sensed torque value falls to zero. FIG. 16B depicts a graph of rotation of knob (130) and torque sensed by sensors (800, 802) during unintentional motion (i.e., trocar (330) is caused to move causing unintentional rotation of knob (130)). As shown in FIG. 16B, rotation of knob (130) is not accompanied by a change in the sensed torque value indicating unintentional motion, i.e., the force applied to circular stapler (10) causing rotation of knob (130) comes from another source other than intentional rotation of knob (130) by the user, such as force created when anvil (400) is attached to trocar (330), although other unintentional forces can be applied. As shown in FIGS. 17A and 17B, sensors (800, 802) can differentiate the direction of unintentional motion based on the direction of rotation of knob (130). FIG. 17A illustrates unintentional retraction of trocar (330) while FIG. 17B illustrates unintentional extension of trocar (330). As discussed below, different levels of feedback can be provided based on the direction of unintentional motion as extension of trocar (330) can create a more dangerous situation due to the sharp distal tip of trocar (330)).

Figure 18:
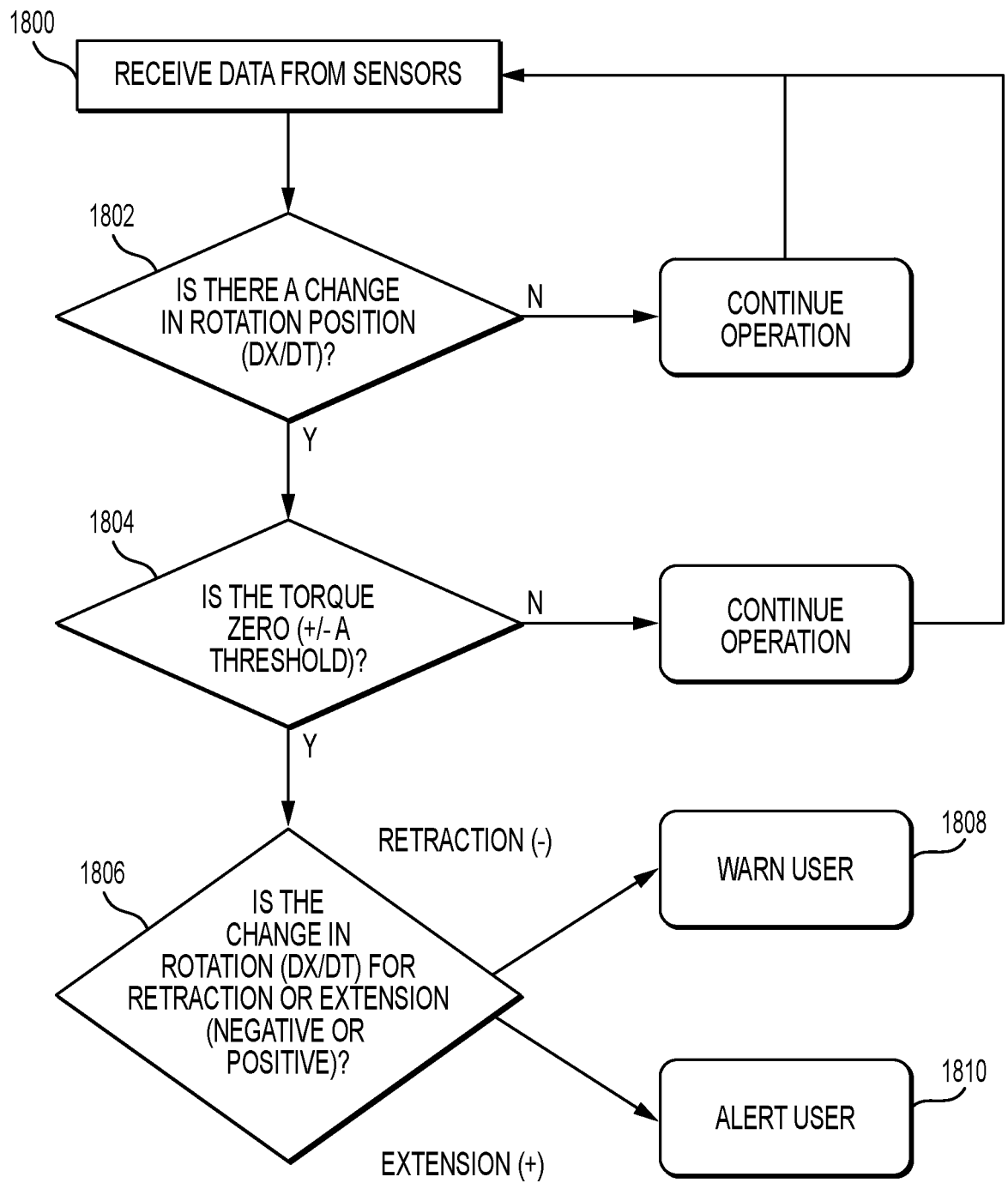
FIG. 18 illustrates a flowchart of a method for determining unintentional motion of the circular stapler shown in FIG. 8A, according to one aspect of the present disclosure.

FIG. 18 illustrates a flowchart of a method for determining unintentional motion using sensors (800, 802). Although the method is described as performed by processor (902) of controller (900), it is to be understood that the method could be performed by one or more processors associated with external hub (908). In step 1800, processor (902) receives data from sensors (800, 802) including rotational data and torque data during operation of circular stapler (10). In step 1802, processor (902) determines whether a change in rotational position of knob (130) is detected. If in step 1802, no rotation is detected the N branch is taken back to step 1800 where operation continues, and processor (902) continues to receive data from sensors (800, 802). If in step 1802, the processor (902) determines that a change in rotational position of knob (130) is detected, the Y branch is taken to step 1804.

In step 1804, processor (902) determines whether the torque value is zero (plus or minus a threshold) during the change in rotational position. If in step 1804, the torque value is not zero (i.e., there is a change in torque (either positive or negative based on the direction of motion) on knob (130) associated with the change in rotational position), processor (902) determines that the motion is intentional (i.e., caused by user rotation of knob (130) during normal operation of circular stapler (10) as shown in FIG. 16A) and the N branch is taken back to step 1800 where operation continues, and processor (902) continues to receive data from sensors (800, 802). If in step 1804, processor (902) determines that the torque level is zero during a change in rotational position of knob (130), the motion is deemed to be unintentional (i.e., unwanted extension or retraction that occurs as a result of an external force on the system not related to user operation of knob (130)) and the Y branch is taken to optional step 1808.

In step 1806, processor (902) determines a direction of the unintentional motion based on the direction of change in the rotational position of knob (130). If in step 1806, processor (902) determines the rotational position change is associated with a retraction of trocar (330), the method proceeds to step 1808 where processor (902) provides a warning to the user. The warning may be provided as haptic or auditory feedback or on indicator (910) of external hub (908). If in step 1806, processor (902) determines the rotational position change is associated with an extension of trocar (330), the method proceeds to step 1810 where processor (902) provides an alert to the user that is more severe than the warning provides in step 1808. The alert may be provided as haptic or auditory feedback or on indicator (910) of external hub (908).

I. Exemplary Determination of Start Condition

In another example, sensors (800, 802), such as torque and rotational sensors, of circular stapler (10) can be utilized to determine a fully closed anvil state for determining a start condition. The start condition can then be used to provide an indicator (910) (either locally on circular stapler (10) or on external hub (908)) to inform the user that the start condition has been reached and that circular stapler (10) is in a condition to fire. In this example, processor (902) of controller (900) can receive data generated by sensors (800, 802) to determine the fully closed anvil state (i.e., when sufficient clamping or tissue compression has occurred). Once the start condition has been determined, processor (902) can provide the indicator (910) that circular stapler (10) is ready to fire. Alternatively, upon determination that the start condition has been met, processor (902) can initiate firing of the circular stapler (10) using controller (900). In other examples, upon determination of the start condition, processor (902) can initiate a timer to provide either the indicator (910) to the user or to directly fire the circular stapler (10) using controller (900) after a time delay. In some examples, circular stapler (10) may be prevented from firing until the start condition is met.

In one example, sensors (800, 802) can provide data used to determine when anvil (400) is fully extended. Processor (902) can use the rotational position of knob (130) to determine the fully closed anvil state when the rotational position of knob (130) has changed from the fully extended position of anvil (400) by more than a threshold amount. Alternatively, the fully closed anvil state can be determined when the change of rotational position of knob (130) is within a particular range of values.

In another example, processor (902) can monitor data received from sensors (800, 802), such as a torque sensor and a rotational position sensor for knob (130), to determine whether the user is actively rotating knob (130). When processor (902) determines that knob (130) is no longer being rotated based on the data from sensors (800, 802), the processor (902) can determine that the start condition has been met and either provide indicator (910) or directly initiate a firing of circular stapler (10). For example, processor (902) can monitor the absolute change in rotational position of knob (130), a percentage shift in rotational position of knob (130), a moving average of the rotational position of knob (130), or a rate of change in rotational position of knob (130). In some examples, when processor (902) determines the start condition, a timer can be set to either provide the indicator (910) or fire circular stapler (10) after a time delay. As shown in FIG. 19, which provides a graph of rotational position of knob (130) over time, a user may rotate knob (130) in a discontinuous fashion. Thus, processor (902) determines lack of change in the rotational position of knob (130) when the user pauses to reset their hand position to turn knob (130). This creates instances as shown in FIG. 19 where the timer is initiated, but subsequent motion occurs. In these cases, the timer resets due to additional rotational motion of knob (130). Once the rotational motion of knob (130) stops the timer restarts. The start condition is not met until there is no motion detected for the entire period of the time. Once the start condition is determined, processor (902) can either provide indicator (910) that circular stapler (10) is ready to be fired or processor (902) can provide instructions to controller (900) to initiate a firing sequence for circular stapler (10). In some examples, circular stapler (10) can prevent a firing until the start condition is determined to have been met, i.e., a lock feature is only removed when the start condition is satisfied.

J. Exemplary Determination of Trocar Position

In another example, sensors (800, 802), such as torque and rotational sensors, of circular stapler (10) can be utilized to determine position of trocar (330) during operation of circular stapler (10). Sensors (800, 802) can be used to monitor torque and rotation of knob (130) based on a zero position, such as the home anvil state determined as described above. Sensors (800, 802) can provide data to controller (900) or to external hub (908) via communication element (906) for determining position of trocar (330) based on the generated data.

Figure 21:
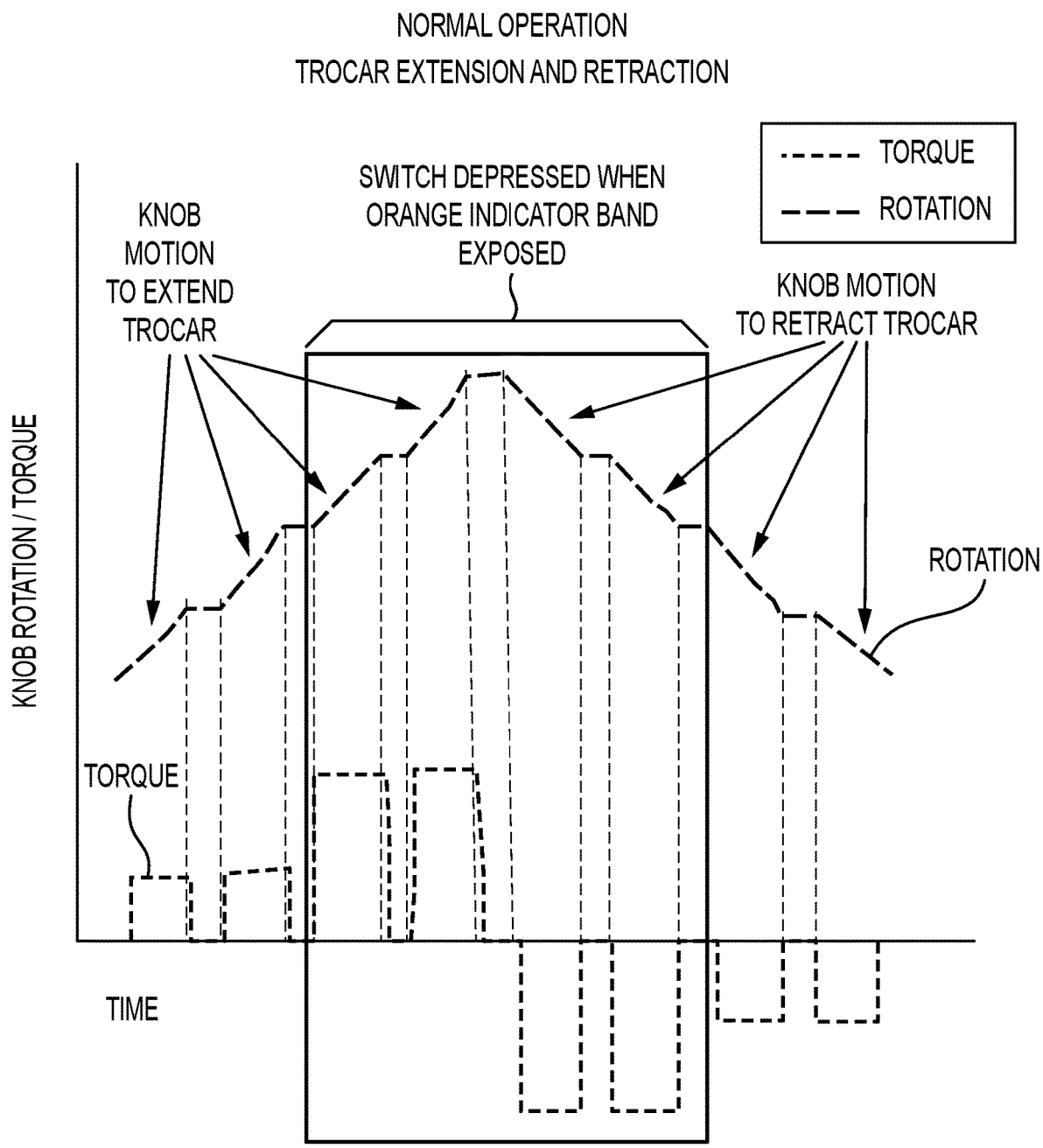
FIG. 21 depicts a graph of knob rotation and torque versus time during operation of the circular stapler shown in FIG. 8A, according to one aspect of the present disclosure.

In one example, torque applied to knob (130) is converted into linear motion of a lead screw that causes translation of trocar (330). As knob (130) rotates, sensors (800, 802) generate data that can be used to determine extension or retraction of trocar (330) based on the amount of torque applied to knob (130). In another example, position of trocar (330) can be correlated to the number of rotations of knob (130) as determined by a rotary encoder based on the known zero position. FIG. 21 illustrates a graph of knob rotation and torque versus time during operation of circular stapler (10). As shown in FIG. 21, rotation of knob (130) is correlated with changes in the sensed torque value. Increases in the sensed torque values or stiffness can indicate when trocar (330) encounters a hard mechanical stop, such as in a fully open or closed position as described herein. In one example, the threads on lead screw that drives trocar (330) can include variable pitches, resulting in a non-linear relationship between turns of knob (130) and movement of trocar (330). A combination of various thread dimensions, lead screw diameters, and switches/sensors (as described herein) could be used to define the exact position of trocar (330) as knob (130) is rotated, enabling the varying pitch to be accounted for when determining position of trocar (330) in accordance with the methods described herein.

Indicator (910) can be used, for example, to provide feedback regarding the position of trocar (330) as correlated to torque and/or rotational position, without relying on visualization by the user of circular stapler (10) itself during operation. In another example, controller (900) (as shown in FIG. 9) receives data from sensors (800, 802) and is configured to determine the position of trocar (330) and provide haptic feedback based on determined positions, such as fully open or fully closed positions of trocar (330).

K. Exemplary Circular Stapler for Sensing of Trocar Position

Figure 24:
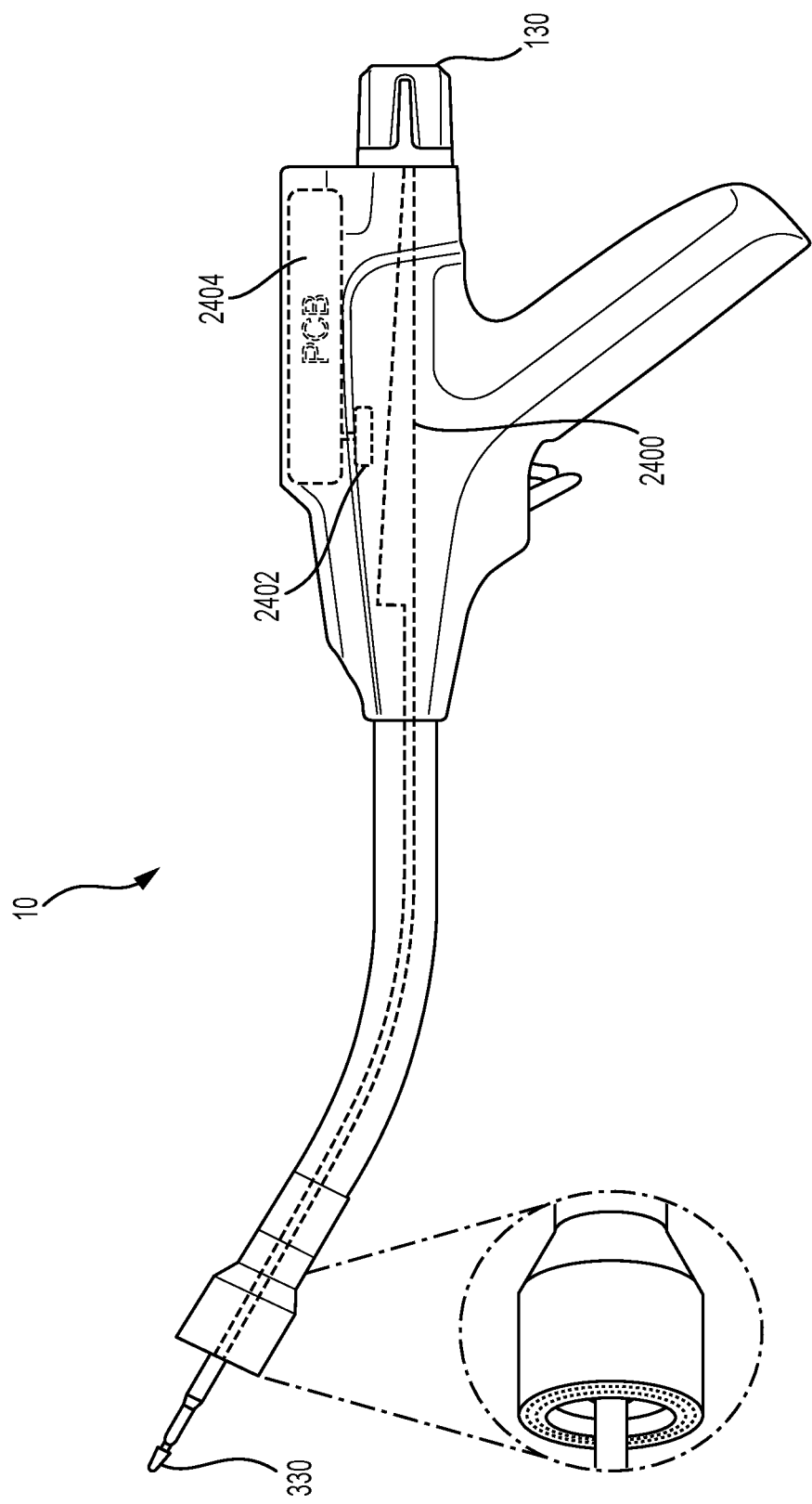
FIG. 24 depicts a circular stapler configured to use capacitive sensing for determining trocar position, according to one aspect of the present disclosure.

FIG. 24 depicts another embodiment of circular stapler (10) for sensing position of trocar (330). In this example, circular stapler (10) includes metal wedge (2400) that extends from the trocar push rod. Metal plate (2402) is held below printed circuit board (2404) adjacent to the trocar push rod. As the push rod translates horizontally, wedge (2400) ascends or descends, respectively, depending on the direction of motion of trocar (330). Movement of wedge (2400) changes the distance of the surface from metal plate (2402). Circular stapler (10) in this example further includes capacitive sensing device configured to measure a change in capacitance based on the distance between wedge (2400) and metal plate (2402), which is correlated to the position of trocar (330).

Figure 25A:
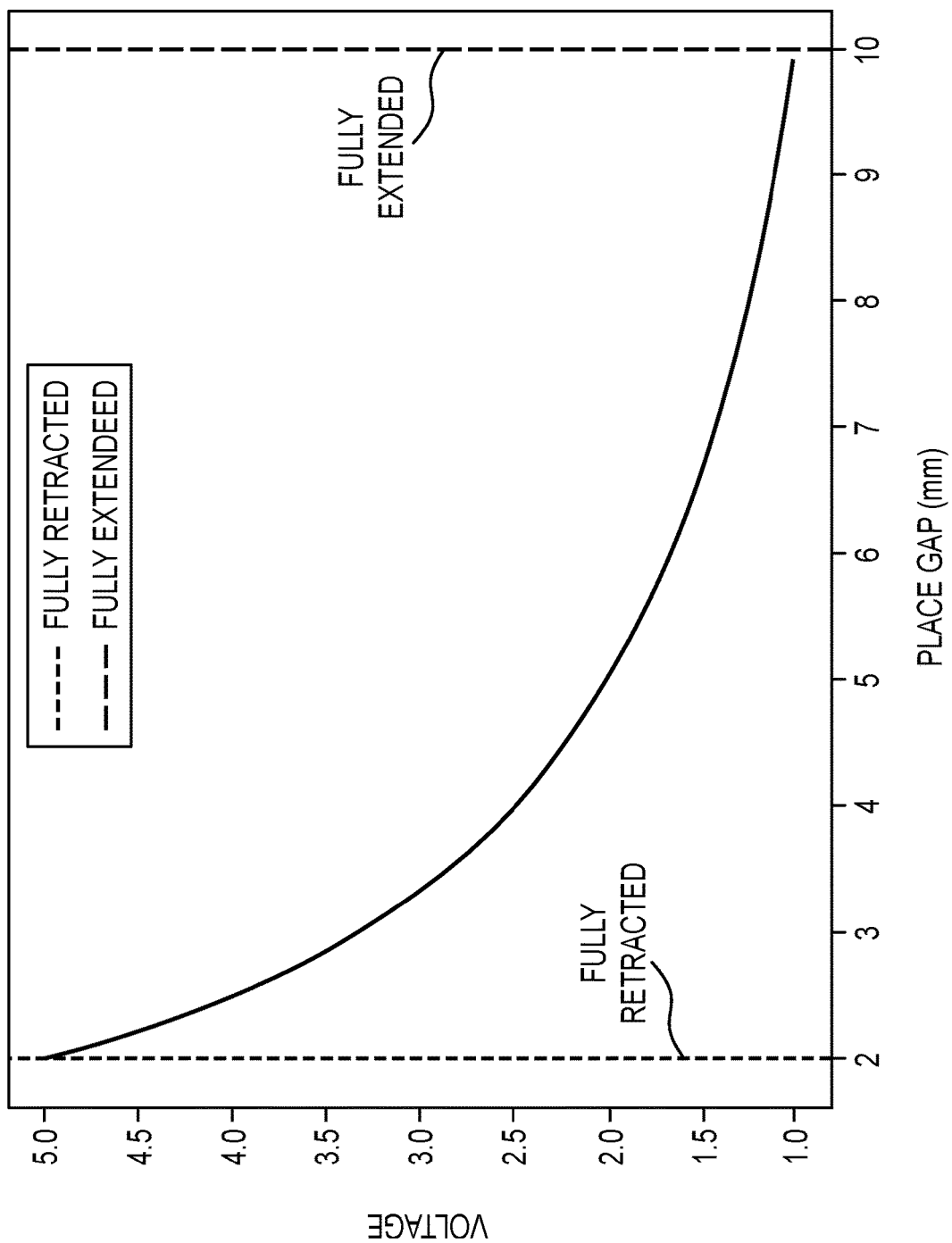
FIG. 25A depicts a graph of potential voltage level versus plate gap during operation of the circular stapler shown in FIG. 24, according to one aspect of the present disclosure.
Figure 25B:
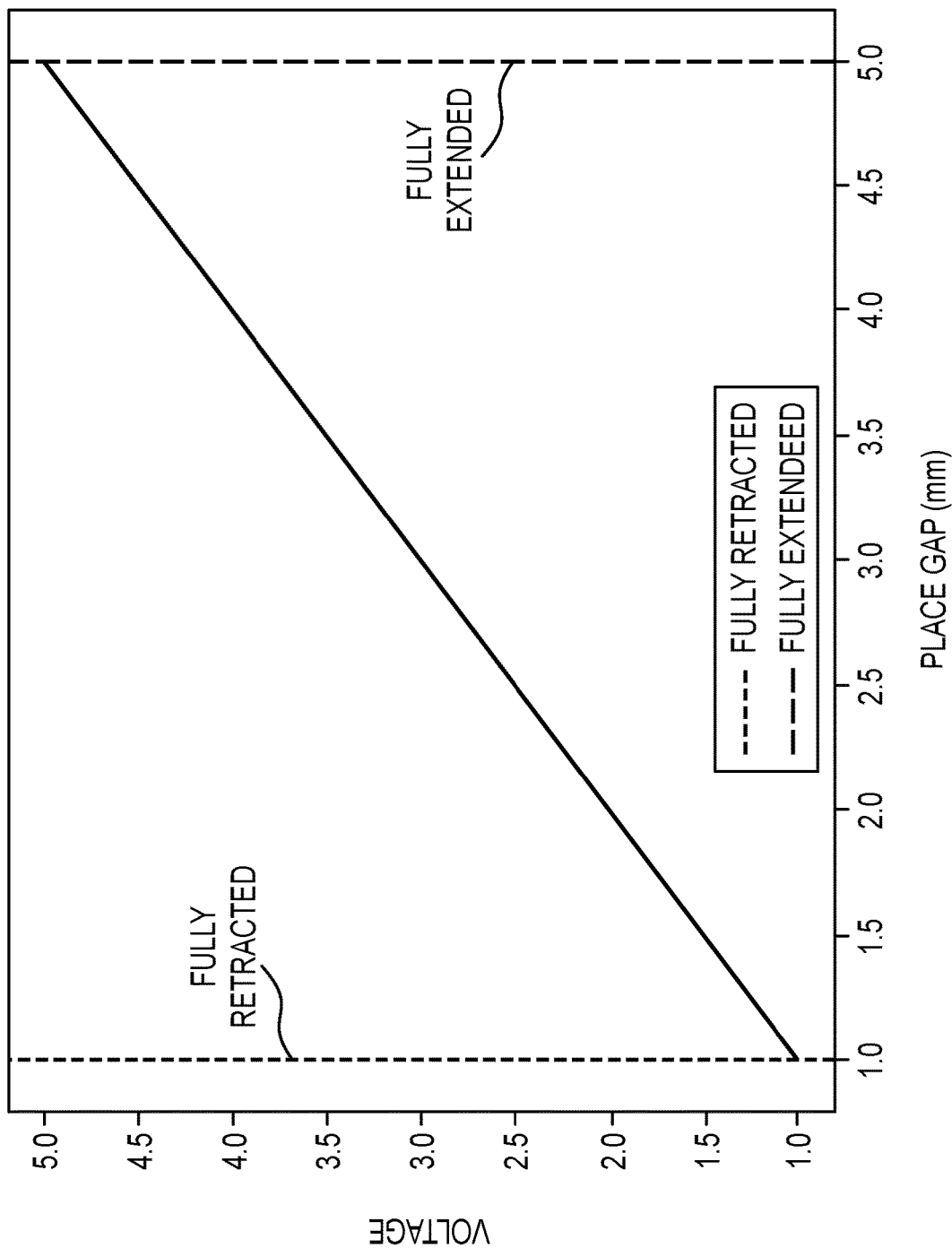
FIG. 25B depicts another graph of potential voltage versus plate gap during operation of the circular stapler shown in FIG. 24, according to one aspect of the present disclosure.

FIG. 25A depicts a plot of potential voltage level of the output signal from capacitive sensing device (2406) in response to movement of the trocar push rod moving trocar (330) between fully retracted and fully extended positions (assuming a 2.0 mm to 10.0 mm gap between wedge (2400) and metal plate (2402). Voltage is calculated using a capacitance level formula where distance provides a multiplicative inverse (1/x) reaction. FIG. 25B is a plot of potential voltage levels for output signals with respect to push rod movement. The linear potentiometer would create a voltage divider, allowing for a 1-to-1 difference in distacne and voltage level.

Figure 26:
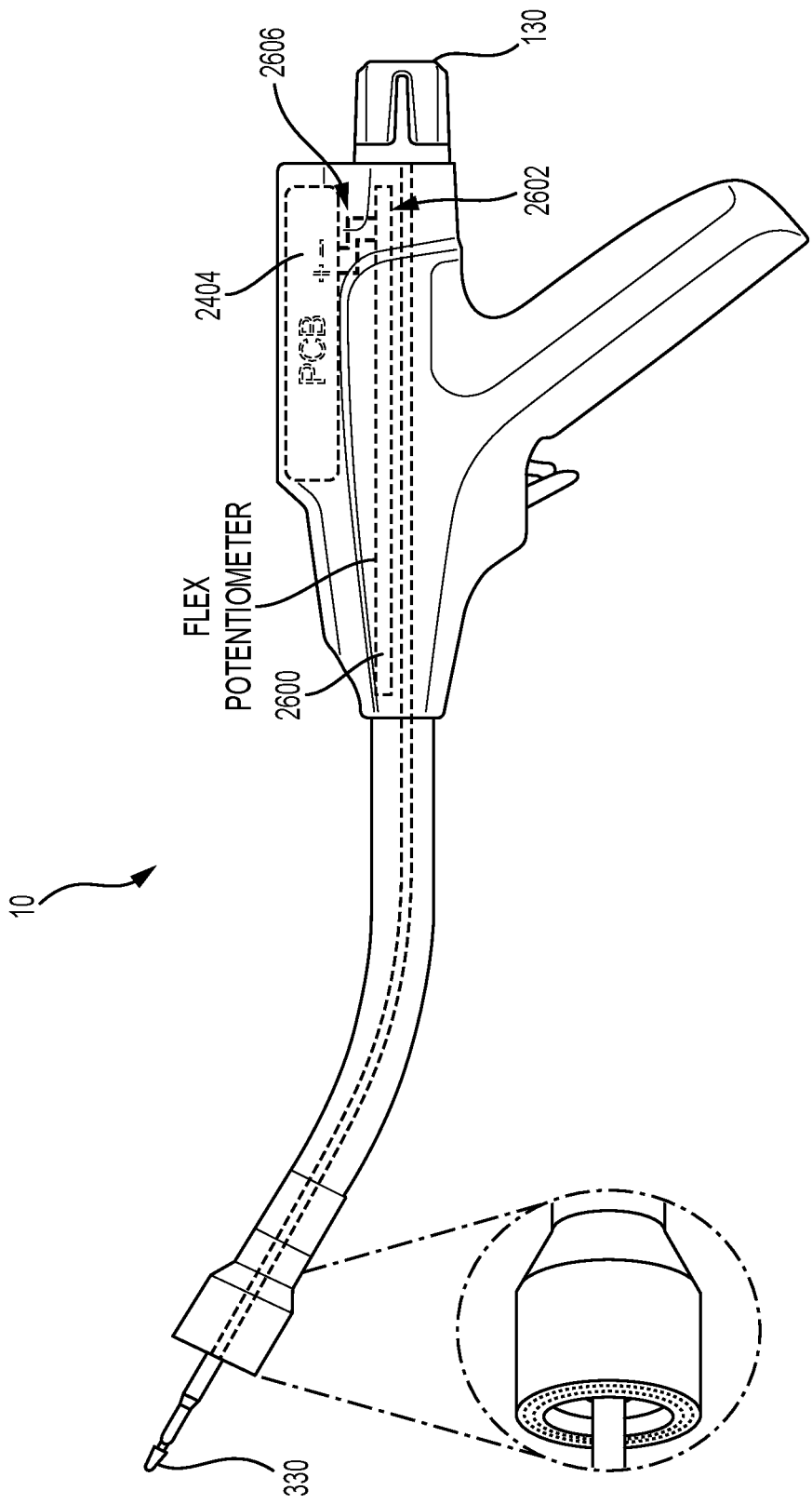
FIG. 26 depicts a circular stapler configured to use resistive sensing for determining trocar position, according to one aspect of the present disclosure.

FIG. 26 depicts another example of circular stapler (10) that utilizes resistive sensing to measure position of trocar (330). In this example, flexible touch-potentiometer (2600) located along the trocar rod and wiper (2602) positioned on the trocar rod. Alternatively, flexible touch-potentiometer (2600) can be located on the trocar rod and wiper (2602) can extend to contact flexible touch-potentiometer (2602). In either example, wiper (2602) provides a force on flexible touch-potentiometer (2600) that varies with movement of the trocar rod, which can be correlated to the position of trocar (330). A sensor can be used to measure the resistance across flexible touch-potentiometer (2600). The sensor can be located on printed circuit board (2404) and is coupled to flexible touch-potentiometer (2600) by flexible cable (2606). The resistance measurement changes based on displacement of trocar (330) due to trocar rod displacement. The change in resistance can be used to determine an absolute measurement of the position of trocar (330) (i.e., distance of movement of trocar (330)).

Figure 27:
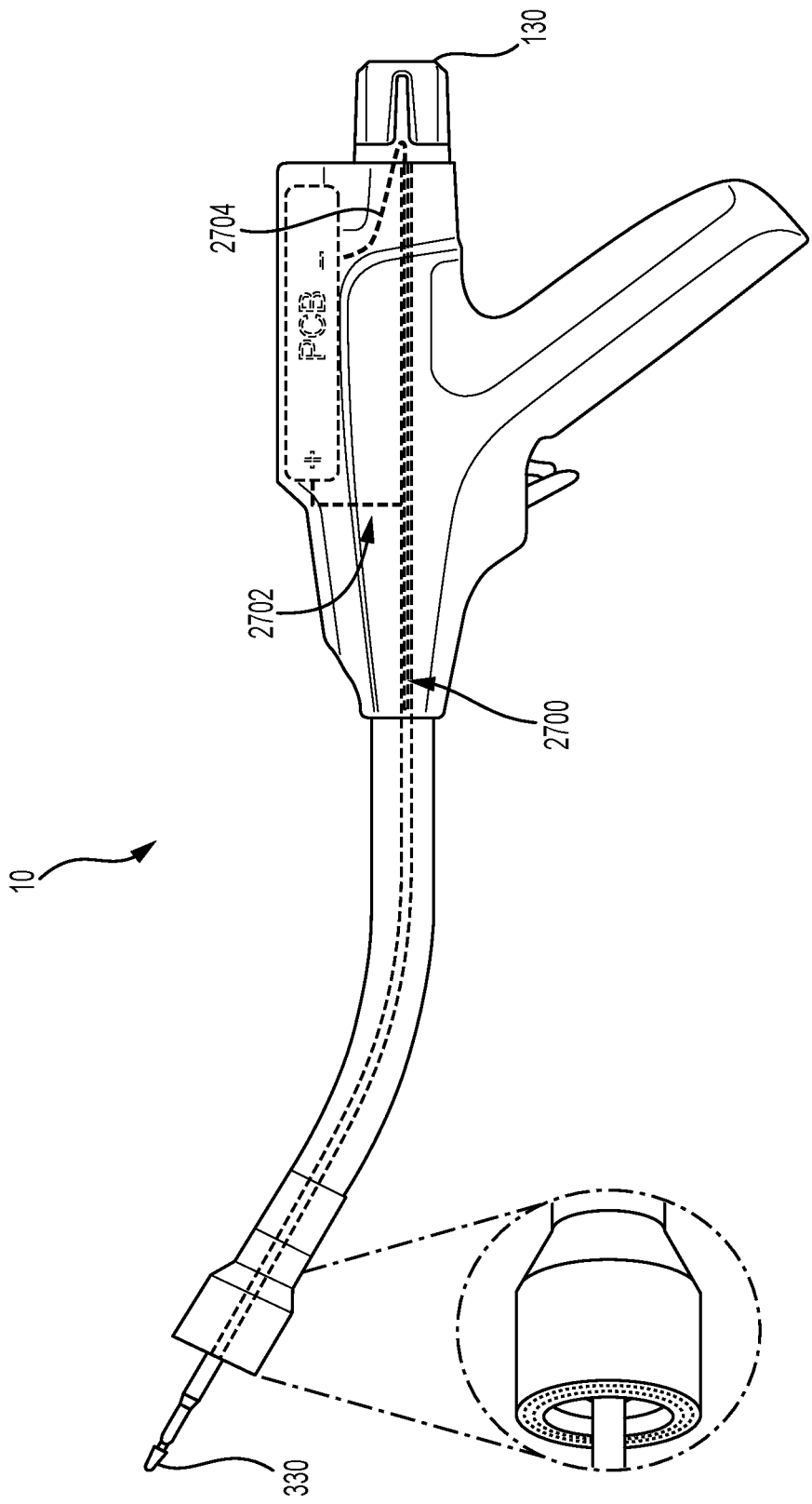
FIG. 27 depicts another circular stapler configured to use resistive sensing for determining trocar position, according to one aspect of the present disclosure.

FIG. 27 depicts another example of circular stapler (10) that includes an electrical printed trace (2700), such as an aerosol jet printed trace located on the trocar rod. Contact (2702) in this example is formed of a conductive material and contact (2704) is formed of a flexible material. As trocar push rod is extended or retracted, a sensor measures the change in resistance across the electrical printed trace (2700), which can be correlated to the change in position of trocar (330). The change in resistance can be used to determine an absolute measurement of the position of trocar (330) (i.e., distance of movement of trocar (330)).

The technology described herein can further be implemented by any of the following numbered clauses:

Clause 1: An apparatus comprising: a stapling head assembly (300); a trocar (330) positioned at least partially within the stapling head assembly (300); an anvil (400) detachably attachable to the trocar (330); a knob (130) rotatable to cause translation of the trocar (330) to adjust a position of the anvil (400) with respect to the stapling head assembly (300); one or more sensors (800, 802) configured to generate data associated with a trocar position or an anvil state; a communication element (906) configured to provide the generated data to a hub (908), wherein the hub (908) is configured to provide an indicator (910) associated with the trocar position or an anvil state based on the generated data.

Clause 2: The apparatus of Clause 1, wherein at least one of the one or more sensors (800, 802) is a torque sensor configured to measure torque applied to the knob (130) or a force sensor configured to measure force based on linear motion.

Clause 3: The apparatus of Clause 2, wherein the knob (130) comprises one or more protrusions (1000) located on an outer circumference (1002) thereof, the apparatus further comprising a fixed element (1004) located partially in a path of the one or more protrusions (1000) as the knob (130) is rotated, wherein the torque sensor measures an increase in the measured torque magnitude when the one or more protrusions (1000) pass the fixed element (1004), wherein the trocar position or anvil state is correlated with a number of the increases in the measured torque magnitude during rotation of the knob (130).

Clause 4: The apparatus of Clause 3, wherein the indicator (910) of the hub (908) displays an open anvil state after a threshold number of increases in the measured torque after a firing of the apparatus.

Clause 5: The apparatus of Clause 2 further comprising one or more protrusions (1100) located on a surface (1102) of a linearly moveable element thereof, the apparatus further comprising a fixed element (1104) located partially in a path of the one or more protrusions (1100) as the linearly moveable element is translated, wherein the sensor measures an increase in the measured torque magnitude or force magnitude when the one or more protrusions (1100) pass the fixed element (1104) and the trocar position or anvil state is based on a number of the increases in the measured torque magnitude or force magnitude, wherein the trocar position or anvil state is correlated with the increases in the torque magnitude or force magnitude measurement.

Clause 6: The apparatus of Clause 5, wherein the fixed element (1104) is positioned such that the indicator (910) of the hub (908) displays an open anvil state based on the increase in the measured torque after a firing of the apparatus.

Clause 7: The apparatus of Clause 5, wherein the fixed element (1104) is positioned such that the indicator (910) of the hub (908) displays a home anvil state based on the increase in the measured torque prior to operation of the apparatus.

Clause 8: The apparatus of Clause 2, wherein at least one of the one or more sensors (800, 802) is a sensor configured to measure a rotational position of the knob (130).

Clause 9: The apparatus of Clause 8, wherein the trocar position or anvil state is correlated to the measured torque during rotation of the knob (130) and the rotational position of the knob (130).

Clause 10: The apparatus of Clause 8 further comprising a controller (900) configured to: receive the generated data associated with the trocar position or anvil state from the one or more sensors (800, 802); determine a fully closed anvil state based on the generated data; and provide an indicator of a start condition for a firing of the apparatus after a time delay based on the determined fully closed anvil state.

Clause 11: The apparatus of Clause 8, wherein the indicator (910) of the hub (908) displays an unintentional motion indicator based on a change in the rotational position of the knob (130) without a corresponding measured magnitude of torque.

Clause 12: The apparatus of Clause 1, wherein the one or more sensors (800, 802) are located in the knob (130).

Clause 13: The apparatus of Clause 1 further comprising: a knob attachment (810) configured to be coupled to the knob (130), wherein one or more of the one or more sensors (800, 802) or the communication element (906) are located in the knob attachment (810).

Clause 14: An apparatus comprising: a stapling head assembly (300); a trocar (330) positioned at least partially within the stapling head assembly (300); an anvil (400) detachably attachable to the trocar (330); a knob (130) rotatable to cause translation of the trocar (330) to adjust a position of the anvil (400) with respect to the stapling head assembly (300); two or more sensors (800, 802) comprising at least a torque sensor configured to measure torque applied to the knob (130) and a sensor configured to measure a rotational position of the knob (130); a controller (900) configured to: receive torque and rotational position data from the two or more sensors (800, 802); and determine a trocar position or an anvil state based on the received torque and rotational position data.

Clause 15: The apparatus of Clause 14, wherein the controller (900) is configured to: determine a number of turns of the knob (130) based on the received torque and rotational position data; and determine the trocar position or anvil state based on the number of turns of the knob (130).

Clause 16: The apparatus of Clause 15, wherein the controller (900) is configured to: determine an open anvil state based on a threshold number of turns of the knob (130) after a firing of the apparatus.

Clause 17: The apparatus of Clause 14, wherein the controller (900) is configured to: determine a fully closed anvil state based on the received torque and rotational position data; and provide an indicator of a start condition for a firing of the apparatus after a time delay based on the determined fully closed anvil state.

Clause 18: The apparatus of Clause 16, wherein the controller (900) is configured to: determine an unintentional motion of the trocar (330) based on a change in the rotational position of the knob (130) without a corresponding measured torque; and provide a user alert based on the determined unintentional motion of the trocar (330).

Clause 19: An apparatus comprising: a stapling head assembly (300) having a staple deck surface (322); a trocar (330) positioned at least partially within the stapling head assembly (300); an anvil (400) having an anvil surface (412) detachably attachable to the trocar (330); a knob (130) rotatable to cause translation of the trocar (330) to adjust a gap between the anvil surface (412) and the staple deck surface (322); a knob attachment (900) configured to be coupled to the knob (130); one or more sensors (800, 802) located in the knob attachment (900) configured to generate data associated with an anvil state based on the gap between the anvil surface (412) and the staple deck surface (322); and a communication element (906) configured to provide the generated data to a hub (908), wherein the hub (908) is configured to provide an indicator (910) associated with the anvil state based on the generated data.

Clause 20: The apparatus of Clause 19, wherein the controller (900) is configured to: determine an unintentional motion of the trocar (330) based on a change in the rotational position of the knob (130) without a corresponding measured torque; and provide a user alert based on the determined unintentional motion of the trocar (330).

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention is not necessarily limited to the examples described, which can be varied in construction and detail. The terms "distal" and "proximal" are used throughout the preceding description and are meant to refer to a positions and directions relative to the physician or user holding circular stapler 10. As such, "distal" or distally" refer to a position distant to or a direction away from the person gripping circular stapler 10. Similarly, "proximal" or "proximally" refer to a position near or a direction towards the person grasping pistol grip 112 (i.e., toward an operator of circular stapler 10). Furthermore, the singular forms "a," "an," and "the" include plural referents unless the context clearly dictates otherwise. Furthermore, the use of "couple", "coupled", or similar phrases should not be construed as being limited to a certain number of components or a particular order of components unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g., "about 90%" may refer to the range of values from 80.001% to 99.999%.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

The invention claimed is:
1. An apparatus comprising:
 a stapling head assembly;
 a trocar positioned at least partially within the stapling head assembly;
 an anvil detachably attachable to the trocar;
 a knob rotatable to cause translation of the trocar to adjust a position of the anvil with respect to the stapling head assembly;
 one or more sensors configured to generate data associated with a trocar position or an anvil state; and
 a communication element configured to provide the generated data to a hub, wherein the hub is configured to provide an indicator associated with the trocar position or an anvil state based on the generated data.
2. The apparatus of claim 1, wherein at least one of the one or more sensors is a torque sensor configured to measure torque applied to the knob or a force sensor configured to measure force based on linear motion.

3. The apparatus of claim 2, wherein the knob comprises one or more protrusions located on an outer circumference thereof, the apparatus further comprising a fixed element located partially in a path of the one or more protrusions as the knob is rotated, wherein the torque sensor measures an increase in the measured torque magnitude when the one or more protrusions pass the fixed element, wherein the trocar position or anvil state is correlated with a number of the increases in the measured torque magnitude during rotation of the knob.

4. The apparatus of claim 3, wherein the indicator of the hub displays an open anvil state after a threshold number of increases in the measured torque after a firing of the apparatus.

5. The apparatus of claim 2 further comprising one or more protrusions located on a surface of a linearly moveable element thereof, the apparatus further comprising a fixed element located partially in a path of the one or more protrusions as the linearly moveable element is translated, wherein the sensor measures an increase in the measured torque magnitude or force magnitude when the one or more protrusions pass the fixed element and the trocar position or anvil state is based on a number of the increases in the measured torque magnitude or force magnitude, wherein the trocar position or anvil state is correlated with the increases in the torque magnitude or force magnitude measurement.

6. The apparatus of claim 5, wherein the fixed element is positioned such that the indicator of the hub displays an open anvil state based on the increase in the measured torque after a firing of the apparatus.

7. The apparatus of claim 5, wherein the fixed element is positioned such that the indicator of the hub displays a home anvil state based on the increase in the measured torque prior to operation of the apparatus.

8. The apparatus of claim 2, wherein at least one of the one or more sensors is a sensor configured to measure a rotational position of the knob.

9. The apparatus of claim 8, wherein the trocar position or anvil state is correlated to the measured torque during rotation of the knob and the rotational position of the knob.

10. The apparatus of claim 8 further comprising a controller configured to:
receive the generated data associated with the trocar position or anvil state from the one or more sensors;
determine a fully closed anvil state based on the generated data; and
provide an indicator of a start condition for a firing of the apparatus after a time delay based on the determined fully closed anvil state.

11. The apparatus of claim 8, wherein the indicator of the hub displays an unintentional motion indicator based on a change in the rotational position of the knob without a corresponding measured magnitude of torque.

12. The apparatus of claim 1, wherein the one or more sensors are located in the knob.

13. The apparatus of claim 1 further comprising:
a knob attachment configured to be coupled to the knob, wherein one or more of the one or more sensors or the communication element are located in the knob attachment.

14. An apparatus comprising:
a stapling head assembly;
a trocar positioned at least partially within the stapling head assembly;
an anvil detachably attachable to the trocar;
a knob rotatable to cause translation of the trocar to adjust a position of the anvil with respect to the stapling head assembly;
two or more sensors comprising at least a torque sensor configured to measure torque applied to the knob and a sensor configured to measure a rotational position of the knob; and
a controller configured to:
receive torque and rotational position data from the two or more sensors; and
determine a trocar position or an anvil state based on the received torque and rotational position data.

15. The apparatus of claim 14, wherein the controller is configured to:
determine a number of turns of the knob based on the received torque and rotational position data; and
determine the trocar position or anvil state based on the number of turns of the knob.

16. The apparatus of claim 15, wherein the controller is configured to:
determine an open anvil state based on a threshold number of turns of the knob after a firing of the apparatus.

17. The apparatus of claim 16, wherein the controller is configured to:
determine an unintentional motion of the trocar based on a change in the rotational position of the knob without a corresponding measured torque; and
provide a user alert based on the determined unintentional motion of the trocar.

18. The apparatus of claim 14, wherein the controller is configured to:
determine a fully closed anvil state based on the received torque and rotational position data; and
provide an indicator of a start condition for a firing of the apparatus after a time delay based on the determined fully closed anvil state.

19. An apparatus comprising:
a stapling head assembly having a staple deck surface;
a trocar (positioned at least partially within the stapling head assembly;
an anvil having an anvil surface detachably attachable to the trocar;
a knob rotatable to cause translation of the trocar to adjust a gap between the anvil surface and the staple deck surface;
a knob attachment configured to be coupled to the knob;
one or more sensors located in the knob attachment configured to generate data associated with an anvil state based on the gap between the anvil surface) and the staple deck surface; and
a communication element configured to provide the generated data to a hub, wherein the hub is configured to provide an indicator associated with the anvil state based on the generated data.

20. The apparatus of claim 19, wherein the controller is configured to: determine an unintentional motion of the trocar based on a change in the rotational position of the knob without a corresponding measured torque; and provide a user alert based on the determined unintentional motion of the trocar.

* * * * *